United States Patent
Jain et al.

(10) Patent No.: US 11,180,522 B2
(45) Date of Patent: Nov. 23, 2021

(54) DISULFIDE-LINKED REVERSIBLE TERMINATORS

(71) Applicant: Centrillion Technology Holdings Corporation, Grand Cayman (KY)

(72) Inventors: Moti Jain, Newark, CA (US); Kendall Hoff, San Francisco, CA (US); Glenn McGall, Palo Alto, CA (US); Wei Zhou, Saratoga, CA (US)

(73) Assignee: Centrillion Technology Holdings Corporation, Grand Cayman (KY)

( * ) Notice: Subject to any disclaimer, the term of this patent is extended or adjusted under 35 U.S.C. 154(b) by 485 days.

(21) Appl. No.: 15/150,166

(22) Filed: May 9, 2016

(65) Prior Publication Data

US 2016/0355541 A1    Dec. 8, 2016

Related U.S. Application Data

(60) Provisional application No. 62/159,017, filed on May 8, 2015.

(51) Int. Cl.
*C07H 19/10* (2006.01)
*C12Q 1/6869* (2018.01)
(Continued)

(52) U.S. Cl.
CPC .............. *C07H 19/10* (2013.01); *C07H 19/14* (2013.01); *C07H 19/20* (2013.01); *C12Q 1/6869* (2013.01); *C12Q 1/6874* (2013.01)

(58) Field of Classification Search
CPC ................. C12Q 1/6869; C12Q 1/6874; C12Q 2525/117; C12Q 2525/186;
(Continued)

(56) References Cited

U.S. PATENT DOCUMENTS

| 3,817,837 A | 6/1974 | Rubenstein et al. |
| 3,850,752 A | 11/1974 | Schuurs et al. |

(Continued)

FOREIGN PATENT DOCUMENTS

| CN | 1617937 A | 5/2005 |
| EP | 1974057 A2 | 10/2008 |

(Continued)

OTHER PUBLICATIONS (R) Buhr et al., "Oligodeoxynucleotides Containing C-7 Propyne Analogs of 7-Deaza-2'-deoxyguanosine and 7-Deaza-2'-deoxyadenosine," Nucleic Acids Research, 24(15),2974-2980 (1996); copy supplied by applicant.*

(Continued)

*Primary Examiner* — Lawrence E Crane
(74) *Attorney, Agent, or Firm* — Wilson Sonsini Goodrich & Rosati

(57) ABSTRACT

The present disclosure provides methods of sequencing polynucleotides and compounds, compositions useful for sequencing of polynucleotides. The chemical compounds include nucleotides and their analogs which possess a sugar moiety comprising a cleavable chemical group capping the 3'-OH group and a base that is attached to a label through a cleavable linker comprising a disulfide bond. In addition, both the disulfide bond and the cleavable chemical group are cleavable by a chemical reagent. Furthermore, after the disulfide bond is cleaved by the chemical reagent, there is no free thiol group linked to the base of the nucleotides according to the fragmentation reaction shown below as an example. Example compounds according to the present disclosure are shown as Formula (I):

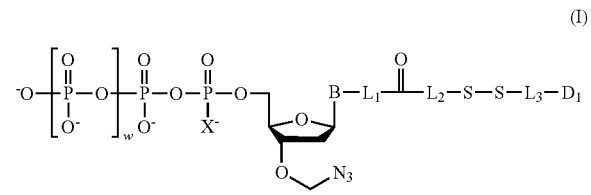

wherein w is 1-5; X is O, S, or $BH_3$; B is a nucleotide base or an analog thereof, $L_{1-3}$ are linkers; and $D_1$ is a label.

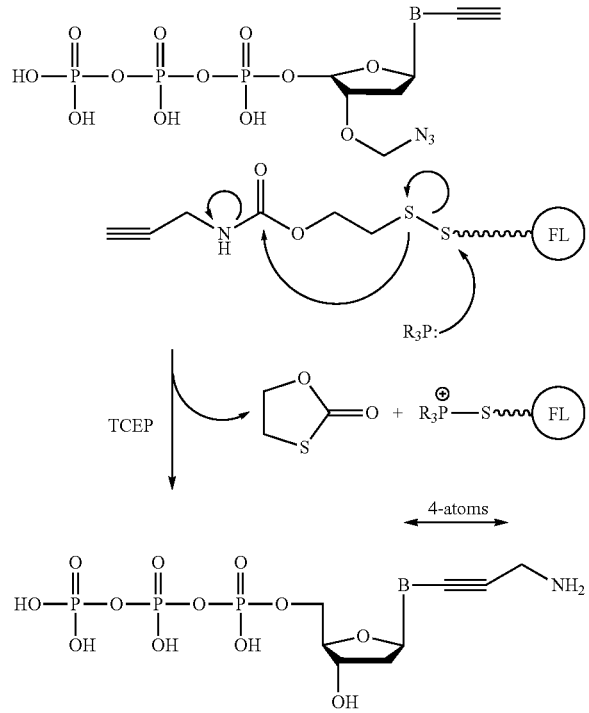

9 Claims, 14 Drawing Sheets
Specification includes a Sequence Listing.

(51) Int. Cl.
   *C07H 19/14* (2006.01)
   *C07H 19/20* (2006.01)
   *C12Q 1/6874* (2018.01)

(58) Field of Classification Search
   CPC .. C12Q 2525/122; C07H 19/10; C07H 19/20; C07H 19/14
   See application file for complete search history.

(56) References Cited

U.S. PATENT DOCUMENTS

| | | | |
|---|---|---|---|
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,971,903 | A | 11/1990 | Hyman |
| 5,302,509 | A | 4/1994 | Cheeseman |
| 5,547,839 | A | 8/1996 | Dower et al. |
| 5,763,594 | A | 6/1998 | Hiatt et al. |
| 5,808,045 | A | 9/1998 | Hiatt et al. |
| 5,872,244 | A | 2/1999 | Hiatt et al. |
| 5,939,292 | A | 8/1999 | Gelfand et al. |
| 6,210,891 | B1 | 4/2001 | Nyren et al. |
| 6,214,987 | B1 | 4/2001 | Hiatt et al. |
| 6,232,465 | B1 | 5/2001 | Hiatt et al. |
| 6,258,568 | B1 | 7/2001 | Nyren |
| 7,057,026 | B2 * | 6/2006 | Barnes ............ 435/287.2 |
| 7,494,791 | B2 * | 2/2009 | Goel ............ A61K 41/00 435/91.2 |
| 7,541,444 | B2 * | 6/2009 | Milton ............ C07H 19/06 435/6.11 |
| 7,771,973 | B2 * | 8/2010 | Milton ............ C07H 19/06 435/6.11 |
| 7,932,034 | B2 | 4/2011 | Esfandyarpour et al. |
| 8,071,739 | B2 * | 12/2011 | Milton ............ C07H 19/06 435/6.11 |
| 8,262,900 | B2 | 9/2012 | Rothberg et al. |
| 8,399,188 | B2 | 3/2013 | Zhao et al. |
| 8,597,881 | B2 * | 12/2013 | Milton ............ C07H 19/06 435/6.1 |
| 8,632,973 | B2 * | 1/2014 | Goel ............ A61K 41/00 435/6.11 |
| 8,808,989 | B1 | 8/2014 | Efcavitch et al. |
| 9,121,060 | B2 * | 9/2015 | Milton ............ C07H 19/06 |
| 9,328,382 | B2 | 5/2016 | Drmanac et al. |
| 9,388,464 | B2 * | 7/2016 | Milton ............ C07H 19/06 |
| 9,650,406 | B2 * | 5/2017 | Zhou ............ C07H 19/10 |
| 2003/0215862 | A1 | 11/2003 | Parce et al. |
| 2005/0130173 | A1 | 6/2005 | Leamon et al. |
| 2006/0134633 | A1 | 6/2006 | Chen et al. |
| 2007/0166705 | A1 | 7/2007 | Milton et al. |
| 2009/0127589 | A1 | 5/2009 | Rothberg et al. |
| 2010/0292452 | A1 | 11/2010 | Milton et al. |
| 2011/0081647 | A1 | 4/2011 | Siddiqi et al. |
| 2014/0186940 | A1 | 7/2014 | Goel |
| 2016/0020691 | A1 | 1/2016 | Yoon et al. |
| 2016/0028802 | A1 | 1/2016 | Balasingh et al. |
| 2016/0046985 | A1 | 2/2016 | Drmanac et al. |
| 2016/0168632 | A1 | 6/2016 | Edwards |
| 2017/0022554 | A1 | 1/2017 | Drmanac et al. |

FOREIGN PATENT DOCUMENTS

| | | |
|---|---|---|
| WO | WO-9321340 A1 | 10/1993 |
| WO | WO-0123411 A2 | 4/2001 |
| WO | WO-2005024010 A1 | 3/2005 |
| WO | WO-2006120433 A1 | 11/2006 |
| WO | WO-2007135368 A2 | 11/2007 |
| WO | WO-2012106546 A2 | 8/2012 |
| WO | WO-2012106546 A3 | 11/2013 |
| WO | WO-2015017759 A1 | 2/2015 |
| WO | WO-2016020691 A1 | 2/2016 |
| WO | WO-2016028802 A1 | 2/2016 |
| WO | WO-2016182984 A1 | 11/2016 |

OTHER PUBLICATIONS

CN 2016103010165 First Office Action dated Mar. 8, 2018 (w/English translation).
Abramova et al., "A facile and effective synthesis of dinucleotide 5' triphosphates," Bioorg. Med. Chem., 15:6549-6555, 2007.
Abramova et al., "Synthesis of morpholine nucleoside triphosphates," Tet. Lett., 45:4361, 2004.
Ansorge et al., Automated DNA sequencing. ultrasensitive detection of fluorescent bands during electrophoresis. Nucl. Acids Res., 15(11):4593-4602, 1987.
Ansorge, Wilhelm J., "Next-generation DNA sequencing techniques," New Biotech., 25(4):195-203, 2009.
Arakawa et al., Novel bioluminescent assay of alkaline phosphatase using adenosine-3-phosphate-5-phosphosulfate as substrate and the luciferin-luciferase reaction and its application. Analytical Biochemistry. 314. 2003. 206-211.
Babendure et al.,Development of a fluorescent probe for the study of nucleosome assembly and dynamics. Anal. Biochem., 317(1):1, 2003.
Burgess et al., "Synthesis of nucleoside triphosphates," Chem. Rev., 100:2047-2059, 2000.
Canard B & Sarfati R., "DNA polymerase fluorescent substrates with reversible 3'-tags," Gene, 148:1-6, 1994.
Caton-Williams J, et al., "Use of a Novel 5'-Regioselective Phosphitylating Reagent for One-Pot Synthesis of Nucleoside 5'-Triphosphates from Unprotected Nucleosides," Current Protocols in Nucleic Acid Chemistry, 2013, 1.30.1-1.30.21.
Connell et al., Automated DNA sequence analysis. BioTechniques, 5(4):342-384, 1987.
Dohm et al., "Substantial biases in ultra-short read data sets from high-throughput DNA sequencing," Nucleic Acids Res., 36:e105, 2008.
Empodocles, et al., Three dimensional orientation measurements of symmetric single chromophores using polarization microscopy. Nature,399:126-130, 1999.
Esfandyarpour et al., "Structural optimization for heat detection of DNA thermosequencing platform using finite element analysis," Biomicrofluidics, 2(2):024102 (1-11), 2008.
European Search Report dated Sep. 14, 2016 for European application No. 16168789.2.
Fuller et al., "The challenges of sequencing by synthesis," Nat. Biotech., 27(11):1013-1023, 2009.
Gardner et al., "Acyclic and dideoxy terminator preferences denote divergent sugar recognition by archaeon and Taq DNA polymerases," Nucl. Acids Res., 30:605-613, 2002.
Hamel et al., "Synthesis of deoxyguanosine polyphosphates and their interactions with the guanosine 5'-triphosphate requiring protein synthetic enzymes of *Escherichia coli*," Biochemistry, 1975, 14(23):5055-5060.
Innis, et al., DNA sequencing with thermus aquatics DNA polymerase and direct sequencing of polymerase chain reaction-amplified DNA. Procedings of the National Academy of sciences of USA. 85; Dec. 1988: 9436-9440.
International Search Report and Written Opinion dated Aug. 5, 2016 for International Application No. PCT/US2016/031416.
Jankowiak et al., Spectroscopic Characterization of the 4-Hydroxy Catechol Estrogen QuinonessDerived GSH and N-Acetylated Cys Conjugates. Chem. Res. Toxicol., 16(3):304, 2003.
Kitayama et al., labels. Photochem. Photobiol., 77(3):333, 2003.
Lacoste et al., Proc. Natl. Acad. Sci. USA, 97(17):9461-9466, 2000.
Lebedev et al., "Preparation of oligodeoxyribonucleotide 5'-triphosphates using solid support approach," Nucleos. Nucleot. Nucleic. Acids, 20: 1403, 2001.
Maeda, M. New label enzymes for bioluminescent enzyme immunoassay. Journal of pharmaceutical and biomedical analysis. 30 (2003). 1725-1734.
Metzker et al., "Termination of DNA synthesis by novel 3'-modified deoxyribonucleoside triphosphates," Nucleic Acids Res.,22:4259-4267, 1994.
Metzker, ML. Sequencing technologies—the next generation. Nat Rev Genet. 2010.11(1):31-46 Epub Dec. 8, 2009. Review.

(56) References Cited

OTHER PUBLICATIONS

Nagata S, et al., "Improved method for the solid-phase synthesis of oligoribonucleotide 5'-triphosphates," Chem. Pharm. Bull., 2012, 60(9):1212-15.

Nishioka et al., "Long and accurate PCR with a mixture of KOD DNA polymerase and its exonuclease deficient mutant enzyme," J. Biotech., 88:141-149, 2001.

Nyren et al., "Enzymatic method for continuous monitoring of inorganic pyrophosphate synthesis," Anal. Biochem.,151:504-509, 1985.

Panchuk, et al., Alexa Dyes, a Series of New Fluorescent Dyes that Yield Exceptionally Bright, Photostable Conjugates. J. Hist. Cyto., 47:1179-1188, 1999.

Prober et al., A System for Rapid DNA Sequencing with Fluorescent Chain-Terminating Dideoxynucleotides. Science, 238:336-341, 1987.

Reichert et al., Chip-Based Optical Detection of DNA Hybridization by means of nanobead labeling. Anal. Chem., 72:6025-6029, 2000.

Roda et al., A Rapid and sensitive 384-well mucrotitre format chemiluminischent enzyme immunoassay for 19-nortestosterone. Luminescence,18(2):72-78. 2003.

Ronaghi, M. Pyrosequencing sheds light on DNA sequencing. Genome Res. Jan. 2001; 11(1): 3-11. Review.

Ruparel et al.,Design and synthesis of a 3-O-allyl photocleavable fluorescent nucleotide as a reversible terminator for DNA sequencing by synthesis. Proc. Natl. Acad. Sci., 102:5932-5937, 2005.

Smith et al., Fluorescence detection in automated DNA sequence analysis. Nature, 321:674, 1986.

Southworth et al., "Cloning of thermostable DNA polymerase from hyperthermophilic marine Archaea with emphasis on *thermococcus* species 9°N-7 and mutations affecting 3'-5' exonuclease activity," Proc. Natl. Acad. Sci. USA, 93(11): 5281-5285, 1996.

Tabor et al., A single residue in DNA polymerases of the *Escherichia coli* DNA polymerase I family is critical for distinguishing between deoxy- and dideoxyribonucleotides. Proc. Natl. Acad. Sci. USA, 92:6339-6343, 1995.

Takagi et al., "Characterization of DNA polymerase from *pyrococcus* sp. strain KOD1 and its application to PCR," App. Env. Microbiol., 63(11):4504-4510, 1997.

Tang, D., Synthesis and application of four fluorescence labeled nucleotides through disulfide as reversible terminators in DNA sequencing by synthesis. Chemical journal of chinese universities. 35; Oct. 17, 2014: 2346-2352.

Turcatti, et al. A new class of cleavable fluorescent nucleotides: synthesis and optimization as reversible terminators for DNA sequencing by synthesis. Nucleic Acids Res. Mar. 2008;36(4):e25.

Vaghefi M., "Chemical synthesis of nucleoside 5'-triphosphates," In: Nucleoside Triphosphates and their Analogs, pp. 1-22, Taylor & Francis, 2005.

Weil et al., Polyphenylene Dendrimers with Different Fluorescent Chromophores Asymmetrically Distributed at the Periphery. J. Am. Chem. Soc., 2001, 123 (33), pp. 8101-8108.

Welch et al., Syntheses of Nucleosides Designed for Combinatorial DNA Sequencing. Chem. Eur. J.,5(3):951-960, 1999.

Wilson et al., Electrochemiluminescence enzyme immunoassay for TNT. Analyst. Apr. 2003. 128: 480-485.

Yin et al., Use of a Green Fluorescent Protein-Based Reporter Fusion for Detection of Nitric Oxide Produced by Denitrifiers. Appl Environ Microbiol.,69(7):3938, 2003.

Zhu et al., Molecular Mechanism Controlling the Incorporation of Fluorescent Nucleotides Into DNA by PCR. Cytometry, 28:206-211, 1997.

EP16168789.2 Office Action dated Nov. 3, 2017.

PCT/US2016/031416 International Preliminary Report on Patentability dated Nov. 14, 2017.

* cited by examiner

Reversible terminators with cleavable disulfide linker

Scheme: Synthesis of New 3'-O-azidomethyl-5-dithio-linked terminators

1. SP_T
2. + dTTP, 2μM (CENT1)
3. + Compound 31, 2μM (EDP)
4. + Compound 31, 2μM (CENT1)
5. + Compound 31, 2μM (CENT1)
   -> + dNTPs, 2μM (CENT1)
6. + Compound 31, 2μM (CENT1)
   -> TCEP
7. + Compound 31, 2μM (CENT1)
   -> TCEP
   -> dCTP, 2μM (CENT1)
8. + Compound 31, 2μM (CENT1)
   -> TCEP
   -> dNTPs, 2μM (CENT1)
9. + dNTPs, 2μM (CENT1)

1. SP_T
2. + dTTP, 2μM (CENT1)
3. + Compound 33, 2μM (CENT1)
4. + Compound 33, 2μM (CENT1)
    -> + dNTP runaway (Bst)
5. + Compound 33, 2μM (CENT1)
    -> TCEP
6. + Compound 33, 2μM (CENT1)
    -> TCEP
    -> + dCTP, 2μM (CENT1)
7. + Compound 33, 2μM (CENT1)
    -> TCEP
    -> + dNTP runaway, 100μM (Bst)
8. + dNTP runaway, 100μM (Bst)

Unstained

SYBR Gold

1. SP_T
2. + dTTP, 2μM (CENT1)
3. + Compound 34, 2μM (CENT1)
4. + Compound 34, 2μM (CENT1)
   -> + dNTP runaway (Bst)
5. + Compound 34, 2μM (CENT1)
   -> TCEP
6. + Compound 34, 2μM (CENT1)
   -> TCEP
   -> + dCTP, 2μM (CENT1)
7. + Compound 34, 2μM (CENT1)
   -> TCEP
   -> + dNTP runaway, 100μM (Bst)
8. + dNTP runaway, 100μM (Bst)

DISULFIDE-LINKED REVERSIBLE TERMINATORS

CROSS-REFERENCE

This application claims the benefit of U.S. Provisional Patent Application No. 62/159,017, filed on May 8, 2015, which is entirely incorporated herein by reference.

SEQUENCE LISTING

The instant application contains a Sequence Listing which has been submitted electronically in ASCII format and is hereby incorporated by reference in its entirety. Said ASCII copy, created on Jun. 28, 2016, is named 38558-719_201_SL.txt and is 756 bytes in size.

BACKGROUND OF THE INVENTION

New sequencing methods, commonly referred to as Next Generation Sequencing (NGS) technologies, have promised to deliver fast, inexpensive and accurate genome information through sequencing. For example, high throughput NGS (HT-NGS) methods may allow scientists to obtain the desired sequence of genes with greater speed and at lower cost. However, sometimes the efficiency of HT-NGS is obtained at the cost of accuracy of the sequencing results. In this context, sequencing by synthesis (SBS) methodologies may allow a more accurate determination of the identity of the incorporated base, thereby offering higher fidelity in HT-NGS. One key step of the SBS methodologies is to place a removable cap at the 3'-OH position of the last nucleotide already in the strand. Accordingly, the synthesis of labeled nucleotides with removable caps at its 3'-OH position is of interest to SBS technologies.

SUMMARY OF THE INVENTION

The present disclosure provides chemical compounds including reversible terminator molecules, i.e. nucleoside and nucleotide analogs which possess a cleavable chemical group covalently attached to the 3' hydroxyl of the nucleotide sugar moiety. In addition, the reversible terminator molecules comprise a detectable label attached to the base of the nucleotide through a cleavable linker. The cleavable linker comprises a disulfide bond which can be cleaved by a chemical reagent at the same time when the same chemical reagent cleaves the cleavable chemical group on the 3' hydroxyl of the nucleotide sugar moiety. The covalent linkage to the 3' hydroxyl is reversible, meaning the cleavable chemical group may be removed by chemical and/or enzymatic processes. The detectable label may optionally be quenchable. The nucleotide analogs may be ribonucleotide or deoxyribonucleotide molecules and analogs, and derivatives thereof. Presence of the covalently bound cleavable chemical group is designed to impede progress of polymerase enzymes used in methods of enzyme-based polynucleotide synthesis.

An aspect of the present disclosure provides a nucleoside 5'-triphosphate analog which has 1) a sugar moiety comprising a cleavable chemical group capping the 3'-OH group of the sugar, and 2) a base that is attached to a detectable label through a cleavable linker. The cleavable linker comprises a disulfide bond. Both the disulfide bond and the cleavable chemical group capping the 3'OH group of the sugar are cleavable by a chemical reagent. Further, after the disulfide bond is cleaved by the chemical reagent, there is no free thiol group linked to the base.

In some embodiments of aspects provided herein, the base of the nucleoside 5'-triphosphate analog is a purine or a pyrimidine. In some embodiments of aspects provided herein, the detectable label of the nucleoside 5'-triphosphate analog is a fluorophore. In some embodiments of aspects provided herein, the base of the nucleoside 5'-triphosphate analog is selected from the group consisting of adenine (A), guanine (G), thymine (T), cytosine (C) and uracil (U). In some embodiments of aspects provided herein, the base of the nucleoside 5'-triphosphate analog is an analog of adenine (A), guanine (G), thymine (T), cytosine (C) or uracil (U).

In some embodiments of aspects provided herein, the sugar moiety of the nucleoside 5'-triphosphate analog is 2-deoxyribose. In some embodiments of aspects provided herein, the chemical reagent used for the cleavage of the nucleoside is 5'-triphosphate analog is trialkylphosphine or triarylphosphine. In some embodiments of aspects provided herein, the chemical reagent used for the cleavage of the nucleoside analog is tris(2-carboxyethyl)phosphine.

In some embodiments of aspects provided herein, the nucleoside 5'-triphosphate analog is formula (I):

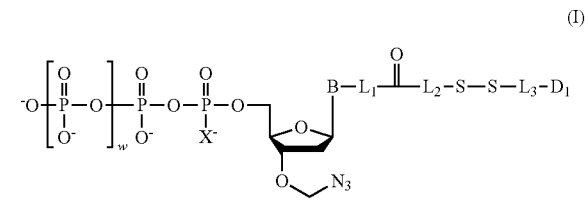

or a salt and/or protonated form thereof, wherein:

X is O, S, or $BH_3$;

w is 1, 2, 3, 4, or 5;

B is a heterocyclic nucleic acid base that is optionally substituted, or an analog thereof;

$L_1$ is a first linker group and $L_1$ is 3-25 atoms in length;

$L_2$ is a second linker group and $L_2$ is 3-4 atoms in length;

$L_3$ is a third linker group and $L_3$ is 4-47 atoms in length; and

D1 is the detectable label.

In some embodiments of aspects provided herein, the nucleoside 5'-triphosphate analog of formula (I) is further defined as:

$L_1$ is

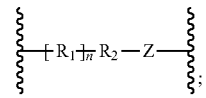

n is 0 or 1;

$R_1$ is

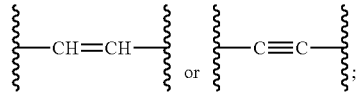

$R_2$ is $$\{\!\!\{-(CH_2)_p-(CH_2-O-CH_2)_q-(CH_2)_r-\}\!\!\}$$

p is 0-3, q is 0-12, r is 1-3; and Z is O or NH.

In some embodiments of aspects provided herein, the nucleoside 5'-triphosphate analog of formula (I) is further defined as:

$L_2$ is $$\{\!\!\{-O-(CH_2)_m-\}\!\!\};$$

and m is 2 or 3.

In some embodiments of aspects provided herein, the nucleoside 5'-triphosphate analog of formula (I) is further defined as:

$L_3$ is $$\{\!\!\{-CH_2-R_3-Q-R_4-Q-\}\!\!\};$$

Q is independently selected from the group consisting of none,

[structures of linker groups containing amide, carbamate, urea, and triazole moieties]

and $R_3$ and $R_4$ are independently $$\{\!\!\{-(CH_2)_p-(CH_2-O-CH_2)_q-(CH_2)_r-\}\!\!\}$$

p is 0-3, q is 0-12, r is 1-3.

In some embodiments of aspects provided herein, the nucleoside 5'-triphosphate analog of formula (I) is further defined as:

B is selected from the group consisting of

[structures of uracil, cytosine, 7-deazaguanine/guanine analog, and 7-deazaadenine/adenine analog nucleobases]

, and

Y is CH or N.

In some embodiments of aspects provided herein, the nucleoside 5'-triphosphate analog of formula (I) is further defined as:

w is 1;

X is O;

$L_1$ is

[propargyl amine, propargyl ether structures], or $$\{\!\!\{-CH_2-O-\}\!\!\};$$

$L_2$ is $$\{\!\!\{-CH_2-CH_2-\}\!\!\};$$

$L_3$ is $$\{\!\!\{-CH_2-CH_2-Q-R_4-Q-\}\!\!\};$$

$R_4$ is $$\{\!\!\{-(CH_2)_p-(CH_2-O-CH_2)_q-(CH_2)_r-\}\!\!\}$$

p is 0-3, q is 0-12, r is 1-3; and

Q is selected from the group consisting of none,

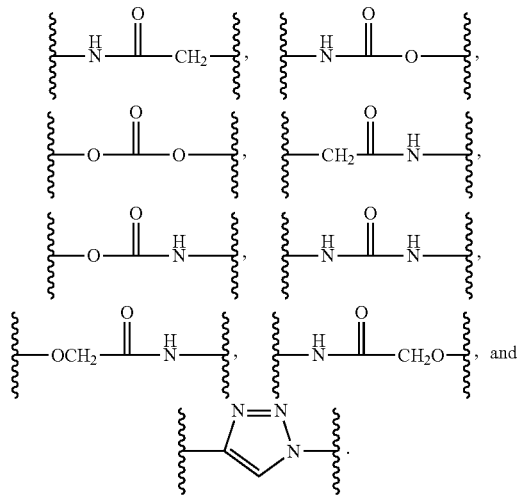

In some embodiments of aspects provided herein, the nucleoside 5'-triphosphate analog of formula (I) is further defined as:

w is 1;
X is O;
$L_1$ is

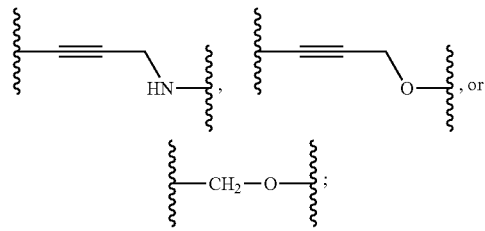

$L_2$ is

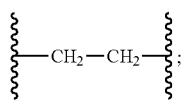

$L_3$ is

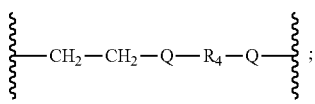

$R_4$ is

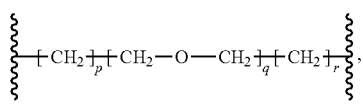

p is 0-3, q is 0-12, r is 1-3; and

Q is selected from the group consisting of none,

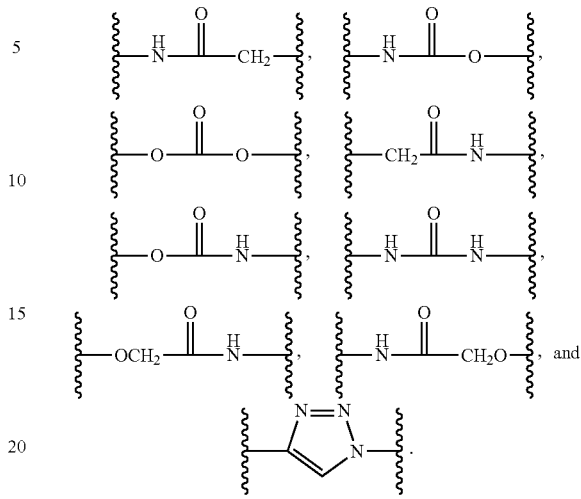

In some embodiments of aspects provided herein, B in formula (I) is selected from the group consisting of adenine (A), guanine (G), thymine (T), cytosine (C) and uracil (U). In some embodiments of aspects provided herein, B in formula (I) is an analog of adenine (A), guanine (G), thymine (T), cytosine (C) or uracil (U). In some embodiments of aspects provided herein, $D_1$ in formula (I) in formula (III) is a fluorophore.

In some embodiments of aspects provided herein, the chemical reagent to cleave the compound of formula (I) is trialkylphosphine or triarylphosphine. In some embodiments of aspects provided herein, the chemical reagent to cleave the compound of formula (I) is tris(2-carboxyethyl)phosphine.

Another aspect of the present disclosure provides a composition. The composition comprises four nucleoside 5'-triphosphates as reversible terminators, wherein each of the 3' positions of the nucleoside 5'-triphosphates is capped with a cleavable chemical group linked to the 3' carbon via an ether linkage. Each of the four nucleoside 5'-triphosphates has a different base, wherein each different base has a different detectable label attached thereto through a cleavable linker. Further, the cleavable linker comprises a disulfide bond. The disulfide bond and the cleavable chemical group at the 3' position are cleavable by a chemical reagent. Because each different reversible terminator may comprise a different detectable label, detection and differentiation of each different type of reversible terminators is achieved. In addition, after the disulfide bond is cleaved by the chemical reagent, there is no free thiol group linked to the different base.

In some embodiments of aspects provided herein for the composition, each different detectable label is a fluorophore. In some embodiments of aspects provided herein for the composition, the chemical reagent is trialkylphosphine or triarylphosphine. In some embodiments of aspects provided herein for the composition, the chemical reagent is tris(2-carboxyethyl)phosphine.

Another aspect of the present disclosure provides a method for sequencing a polynucleotide, comprises:
performing a polymerization reaction in a reaction system comprising a target polynucleotide to be sequenced, one or more polynucleotide primers which hybridize with the target polynucleotide to be sequenced, a catalytic amount of a polymerase enzyme and one or more nucleoside 5'-triphosphates analogs disclosed in the present disclosure.

In some embodiments of aspects provided herein for the sequencing method, the one or more 5'-triphosphate analogs are at a concentration of no more than 400 µM. In some embodiments of aspects provided herein for the sequencing method, the one or more 5'-triphosphate analogs are at a concentration of no more than 100 µM. In some embodiments of aspects provided herein for the sequencing method, the one or more 5'-triphosphate analogs are at a concentration of no more than 50 µM. In some embodiments of aspects provided herein for the sequencing method, the one or more 5'-triphosphate analogs are at a concentration of no more than 10 In some embodiments of aspects provided herein for the sequencing method, the one or more 5'-triphosphate analogs are at a concentration of no more than 5 µM. In some embodiments of aspects provided herein for the sequencing method, the one or more 5'-triphosphate analogs are at a concentration of no more than 3 µM. In some embodiments of aspects provided herein for the sequencing method, the one or more 5'-triphosphate analogs are at a concentration of no more than 2 µM.

Still another aspect of the present disclosure provides a method of sequencing a polynucleotide. The sequencing method comprises: performing a polymerization reaction in a reaction system comprising a target polynucleotide to be sequenced, one or more polynucleotide primers which hybridize with the target polynucleotide to be sequenced, a catalytic amount of a polymerase enzyme and one or more nucleoside 5'-triphosphate analogs disclosed in the present disclosure; and treating products of the polymerization reaction with a solution of trialkylphosphine.

In some embodiments of aspects provided herein for the sequencing method, the trialkylphosphine used is tris(2-carboxyethyl)phosphine. In some embodiments of aspects provided herein for the sequencing method, after treatment with the solution of trialkylphosphine, the one or more nucleoside 5'-triphosphate analogs of claim 1 do not have free thiol group linked to their bases.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
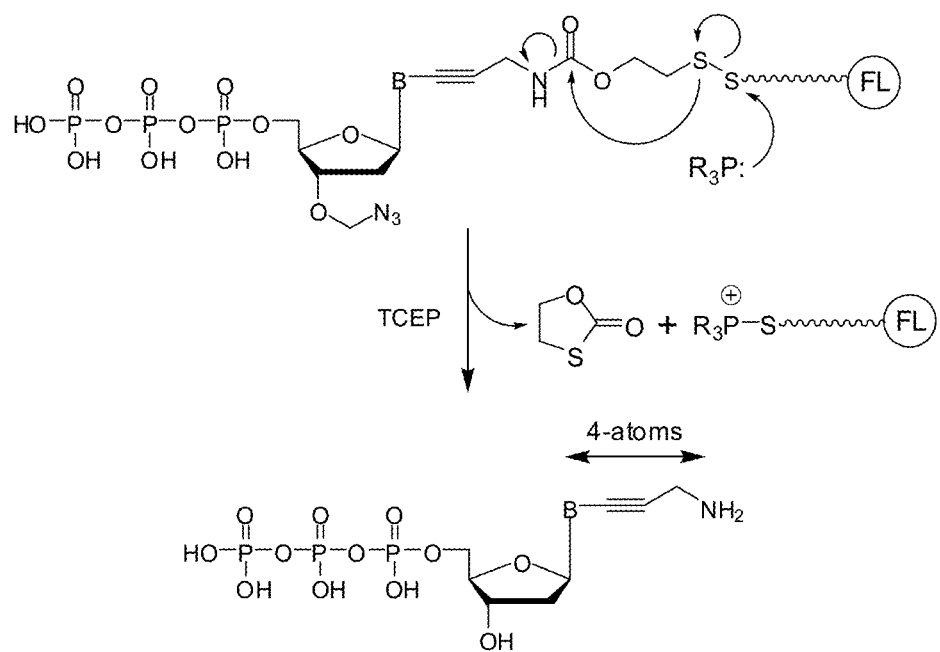
FIG. 1 illustrates a possible mechanism for a trialkylphosphine to cleave the disulfide bond and the cleavable linker on 3'-OH of a reversible terminator disclosed in the present disclosure.

The second generation sequencing (NGS) approaches, involving sequencing by synthesis (SBS) have experienced a rapid development as data produced by these new technologies mushroomed exponentially. The cyclic reversible technology involves incorporation of reversible terminators, fluorescence imaging and cleavage. The reversible terminators successfully employed may have either 3' blocking groups, 3'O-allyl (Intelligent bio) or 3'-O-azidomethyl—dNTP's (Illumina) while the label is linked to the base, which act as a reporter and can be cleaved. The other type is 3'-unblocked reversible terminators in which terminator group is linked to the base as well as fluorescence group which not only act as a reporter but also act as reversible terminating group.

The major issue with most NGS is short read length of 50-150 bases. One of the fundamental reasons for the short read length in cyclic reversible technology is reversible terminators developed so far leave behind a long scar (6-10 atoms) after cleavage of the linker carrying the fluorophore. Accumulation of such scars along the major grove of the DNA complex impaired the stability of DNA double helix structure adversely, thereby hindering the substrate recognition and primer extension.

Therefore, there is a need to develop nucleotide analogs that work well with polymerase enzymes and are able to terminate strand growth upon incorporation into the growing strand. A pause in polymerase activity during strand elongation caused by a reversible terminator nucleotide analog allows accurate determination of the identity of the incorporated nucleic acid. Ability to continue strand synthesis after this accurate determination is made would be ideal, through subsequent modification of the reversible terminator nucleotide analog that allows the polymerase enzyme to continue to the next position on the growing DNA strand. The process of arresting DNA polymerization followed by removal of the blocking group on the incorporated non-native nucleotide is referred to herein as sequential reversible termination. Another requirement of sequential reversible termination is that the non-native nucleotide analog must be easily removed without damaging the growing DNA strand or the polymerase, i.e. termination must be reversible under mild reaction conditions. Still another goal of the present disclosure is to find a chemical reagent to cleave both the detectable label attached on the incorporated nucleotide and the blocking group on the incorporated non-native nucleotide.

Sequencing-by-Synthesis (SBS) and Single-Base-Extension (SBE) Sequencing

Several techniques are available to achieve high-throughput sequencing. (See, Ansorge; Metzker; and Pareek et al., "Sequencing technologies and genome sequencing," *J. Appl. Genet.*, 52(4):413-435, 2011, and references cited therein). The SBS method is a commonly employed approach, coupled with improvements in PCR, such as emulsion PCR (emPCR), to rapidly and efficiently determine the sequence of many fragments of a nucleotide sequence in a short amount of time. In SBS, nucleotides are incorporated by a polymerase enzyme and because the nucleotides are differently labeled, the signal of the incorporated nucleotide, and therefore the identity of the nucleotide being incorporated into the growing synthetic polynucleotide strand, are determined by sensitive instruments, such as cameras.

SBS methods commonly employ reversible terminator nucleic acids, i.e. bases which contain a covalent modification precluding further synthesis steps by the polymerase enzyme once incorporated into the growing stand. This covalent modification can then be removed later, for instance using chemicals or specific enzymes, to allow the next complementary nucleotide to be added by the polymerase. Other methods employ sequencing-by-ligation techniques, such as the Applied Biosystems SOLiD platform technology. Other companies, such as Helicos, provide technologies that are able to detect single molecule synthesis in SBS procedures without prior sample amplification, through use of very sensitive detection technologies and special labels that emit sufficient light for detection. Pyrosequencing is another technology employed by some commercially available NGS instruments. The Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.*, 151:504-509, 1985; see also, U.S. Patent Application Publication Nos. 2005/0130173 and 2006/0134633; U.S. Pat. Nos. 4,971,903, 6,258,568 and 6,210,891).

Sequencing using the presently disclosed reversible terminator molecules may be performed by any means available. Generally, the categories of available technologies include, but are not limited to, sequencing-by-synthesis (SBS), sequencing by single-base-extension (SBE), sequencing-by-ligation, single molecule sequencing, and pyrosequencing, etc. The method most applicable to the present compounds, compositions, methods and kits is SBS. Many commercially available instruments employ SBS for determining the sequence of a target polynucleotide. Some of these are briefly summarized below.

One method, used by the Roche Applied Science 454 GenomeSequencer, involves detection of pyrophosphate (pyrosequencing). (See, Nyren et al., "Enzymatic method for continuous monitoring of inorganic pyrophosphate synthesis," *Anal. Biochem.*, 151:504-509, 1985). As with most methods, the process begins by generating nucleotide fragments of a manageable length that work in the system employed, i.e. about 400-500 bp. (See, Metzker, Michael A., "Sequencing technologies—the next generation," *Nature Rev. Gen.*, 11:31-46, 2010). Nucleotide primers are ligated to either end of the fragments and the sequences individually amplified by binding to a bead followed by emulsion PCR. The amplified DNA is then denatured and each bead is then placed at the top end of an etched fiber in an optical fiber chip made of glass fiber bundles. The fiber bundles have at the opposite end a sensitive charged-couple device (CCD) camera to detect light emitted from the other end of the fiber holding the bead. Each unique bead is located at the end of a fiber, where the fiber itself is anchored to a spatially-addressable chip, with each chip containing hundreds of thousands of such fibers with beads attached. Next, using an SBS technique, the beads are provided a primer complementary to the primer ligated to the opposite end of the DNA, polymerase enzyme and only one native nucleotide, i.e., C, or T, or A, or G, and the reaction allowed to proceed. Incorporation of the next base by the polymerase releases light which is detected by the CCD camera at the opposite end of the bead. (See, Ansorge, Wilhelm J., "Next-generation DNA sequencing techniques," *New Biotech.*, 25(4):195-203, 2009). The light is generated by use of an ATP sulfurylase enzyme, inclusion of adenosine 5' phosphosulferate, luciferase enzyme and pyrophosphate. (See, Ronaghi, M., "Pyrosequencing sheds light on DNA sequencing," *Genome Res.*, 11(1):3-11, 2001).

A commercially available instrument, called the Genome Analyzer, also utilizes SBS technology. (See, Ansorge, at page 197). Similar to the Roche instrument, sample DNA is first fragmented to a manageable length and amplified. The amplification step is somewhat unique because it involves formation of about 1,000 copies of single-stranded DNA fragments, called polonies. Briefly, adapters are ligated to both ends of the DNA fragments, and the fragments are then hybridized to a surface having covalently attached thereto primers complimentary to the adapters, forming tiny bridges on the surface. Thus, amplification of these hybridized fragments yields small colonies or clusters of amplified fragments spatially co-localized to one area of the surface. SBS is initiated by supplying the surface with polymerase enzyme and reversible terminator nucleotides, each of which is fluorescently labeled with a different dye. Upon incorporation into the new growing strand by the polymerase, the fluorescent signal is detected using a CCD camera. The terminator moiety, covalently attached to the 3' end of the reversible terminator nucleotides, is then removed as well as the fluorescent dye, providing the polymerase enzyme with a clean slate for the next round of synthesis. (Id., see also, U.S. Pat. No. 8,399,188; Metzker, at pages 34-36).

Many SBS strategies rely on detection of incorporation of detectably labeled nucleotides and nucleotide analogs. Such detection may rely on fluorescence or other optical signal, but this is not a requirement. Other technologies available are targeted towards measuring changes in heat and pH surrounding the nucleotide incorporation event. (See, U.S. Pat. Nos. 7,932,034 and 8,262,900; U.S. Patent Application Publication No. 20090127589; and Esfandyarpour et al., "Structural optimization for heat detection of DNA thermosequencing platform using finite element analysis," *Biomicrofluidics*, 2(2):024102 (1-11), 2008). Ion Torent, a Life Technologies company, utilizes this technology in their ion sensing-based SBS instruments. In the Ion Torrent instrument, field effect transistors (FETs) are employed to detect minute changes in pH in microwells where the SBS polymerase reaction is occurring. Each well in the microwell array is an individual single molecule reaction vessel containing a polymerase enzyme, a target/template strand and the growing complementary strand. Sequential cycling of the four nucleotides into the wells allows FETs aligned below each microwell to detect the change in pH as the nucleotides are incorporated into the growing DNA strand. FETs convert this signal into a change in voltage, the change being commensurate in magnitude with the total number of nucleotides incorporated in that synthesis step.

In SBS-based NGS methods, reversible terminator nucleotides are key to the success of obtaining the identity of the polynucleotide target sequence in an efficient and accurate manner. The present reversible terminators may be utilized in any of these contexts by substitution for the nucleotides and nucleotide analogs previously described in those methods. That is, the substitution of the present reversible terminators may enhance and improve all of these SBS and SBE methods. The majority of these protocols utilize deoxyribonucleotide triphosphates, or dNTPs. Likewise, the present reversible terminators may be substituted in dNTP form. Other forms of the present reversible terminators useful in other methodologies for sequencing are described below.

Reversible Terminator Nucleotides

The process for using reversible terminator molecules in the context of SBS, SBE and like methodologies generally involves incorporation of a labeled nucleotide analog into the growing polynucleotide chain, followed by detection of the label, then cleavage of the nucleotide analog to remove the covalent modification blocking continued synthesis. The cleaving step may be accomplished using enzymes or by chemical cleavage. Modifications of nucleotides may be made on the 5' terminal phosphate or the 3' hydroxyl group. Developing a truly reversible set of nucleotide terminators has been a goal for many years. Despite the recent advances only a few solutions have been presented, most of which cause other problems, including inefficient or incomplete incorporation by the polymerase, inefficient or incomplete cleavage of the removable group, or harsh conditions needed to for the cleaving step causing spurious problems with the remainder of the assay and/or fidelity of the target sequence. In a standard SBS protocol using reversible terminators, the polymerase enzyme has to accommodate obtrusive groups on the nucleotides that are used for attachment of fluorescent signaling moiety, as well as blocking groups on the 3'-OH. Native polymerases have a low tolerance for these modifications, especially the 3'-blocking groups. Mutagenesis of polymerase enzymes is necessary to obtain enzymes with acceptable incorporation efficiencies. After cleaving the fluorophore from the base, many current methodologies leave an unnatural "scar" on the remaining nucleobase. (See, for instance, Metzker, Michael A., "Sequencing technologies—the next generation," *Nature Rev. Gen.*, 11:31-46, 2010 and Fuller et al., "The challenges of sequencing by synthesis," *Nat. Biotech.*, 27(11):1013-1023, 2009).

Thus, a limited number of groups suitable for blocking the 3'-oxygen have been shown to be useful when used in combination with certain mutant polymerases which allow the enzyme to tolerate modifications at the 3'-position. These include azidomethyl, allyl and allyloxycarbonyl. (See, for example, Metzker et al., "Termination of DNA synthesis by novel 3'-modified deoxyribonucleoside triphosphates," *Nucleic Acids Res.*, 22:4259-4267, 1994; and U.S. Pat. Nos. 5,872,244; 6,232,465; 6,214,987; 5,808,045; 5,763,594, and 5,302,509; and U.S. Patent Application Publication No. 20030215862). These groups require the application of chemical reagents to effect cleavage. Carboxylic esters, carbonates or thiocarbonate groups at the 3'-position have proven too labile to be effective as chain terminators, ostensibly due to an intrinsic editing activity of the polymerase distinct from exonuclease activity. (See, Canard B & Sarfati R., "DNA polymerase fluorescent substrates with reversible 3'-tags," *Gene*, 148:1-6, 1994).

We report herein a new class of fluorescently labeled reversible terminators.

The new class of fluorescently labeled reversible terminators has a 3'-azidomethyl blocking group and a disulfanylalkoxycarbonylamino linked fluorophore tags to the bases. Exposing the terminators with reducing agent such as tris(2-carboxyethyl)phosphine (TCEP), will not only cleave the 3'-azidomethyl function, but also reduce the disulfide bond, triggering the simultaneous cleavage of the carbamate bond by intra-molecular cyclization of the resulting sulfide anion. More importantly, the cleavage of the fluorophore will leave only a small (4-atoms) scar on the base and will also eliminate highly reactive thiol-terminal functions often associated with disulfide cleavage on the bases (FIG. 1). DNA sequences are determined by the unique fluorescence emission of the cleaved fluorophores and simultaneous removal of the azidomethyl group regenerates 3'-OH function for further polymerase extension reactions.

It should be noted that although FIG. 1 illustrates a proposed mechanism through which the reversible terminator of the present disclosure can react with a trialkylphosphine, a similar mechanism is also possible when the reversible terminator is incorporated into a DNA or RNA strand. In that case, the triphosphate moiety of the reversible terminator shown in FIG. 1 will be replaced with a phosphodiester bond linkage to the end of a DNA or RNA strand. Accordingly, because the 3'-OH group of the reversible terminator is capped by the azidomethyl group, the DNA or RNA strand growth will terminate or stop. However, when treated with trialkylphosphine, such as TCEP, both the fluorophore attached to the base and the capping moiety on the 3'-OH group of the sugar will be cleaved, similar to what has been illustrated above. The exposed 3'-OH group of the incorporated reversible terminator on the end of the DNA or RNA strand will allow continued strand growth of the DNA and RNA.

Further, although the reversible terminator shown in FIG. 1 is a triphosphate, other analogs of triphosphate are allowed at the 5' position of the nucleotide, as shown elsewhere in this disclosure.

Figure 2:
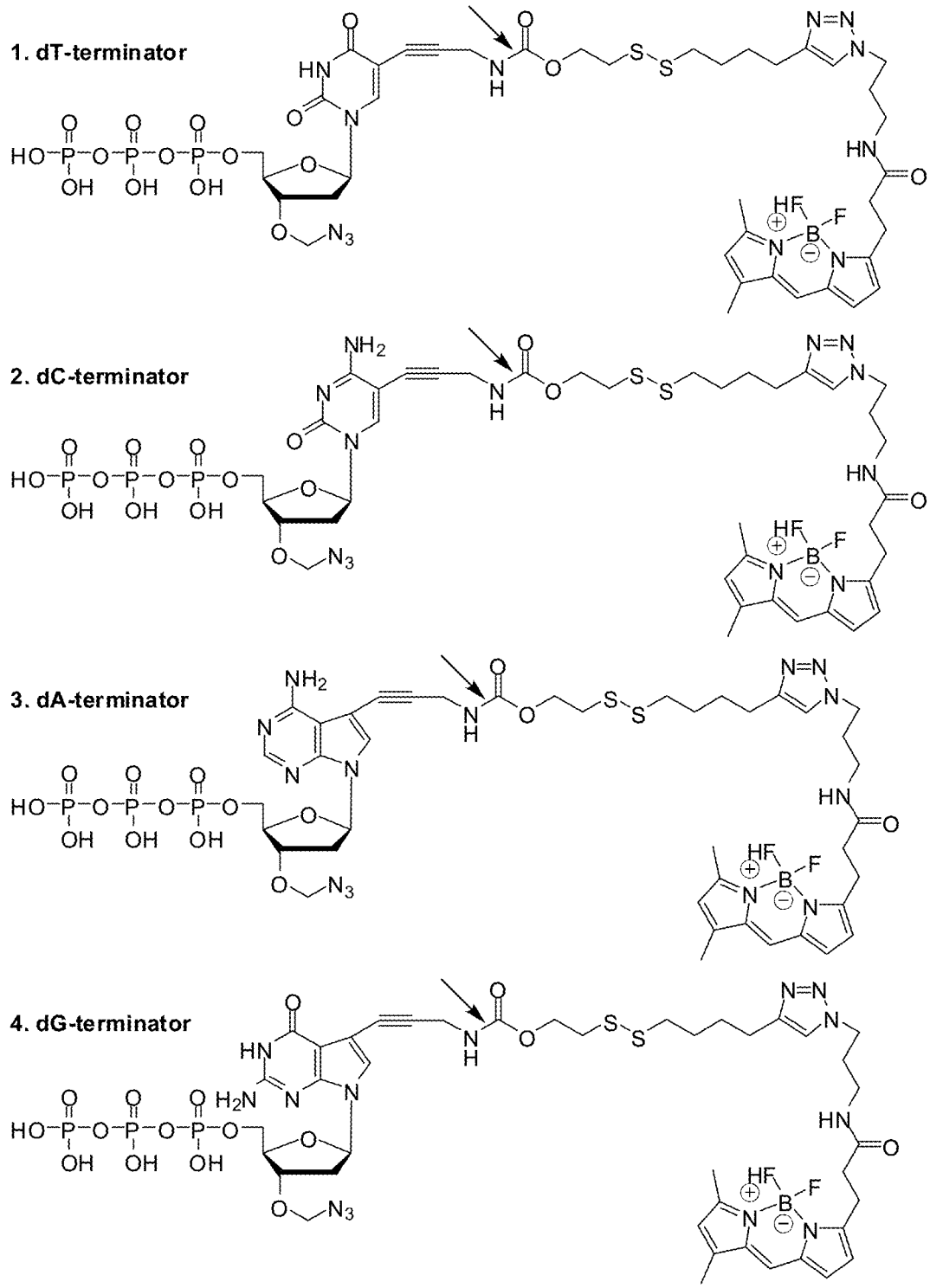
FIG. 2 illustrates nucleotide terminators of the present disclosure with deoxyribose as the sugar and thymine/uracil, adenine, cytidine and guanine as the base. These reversible terminators can be prepared using similar chemistry as provided herein to afford labeled nucleotide terminators.
Figure 3A:
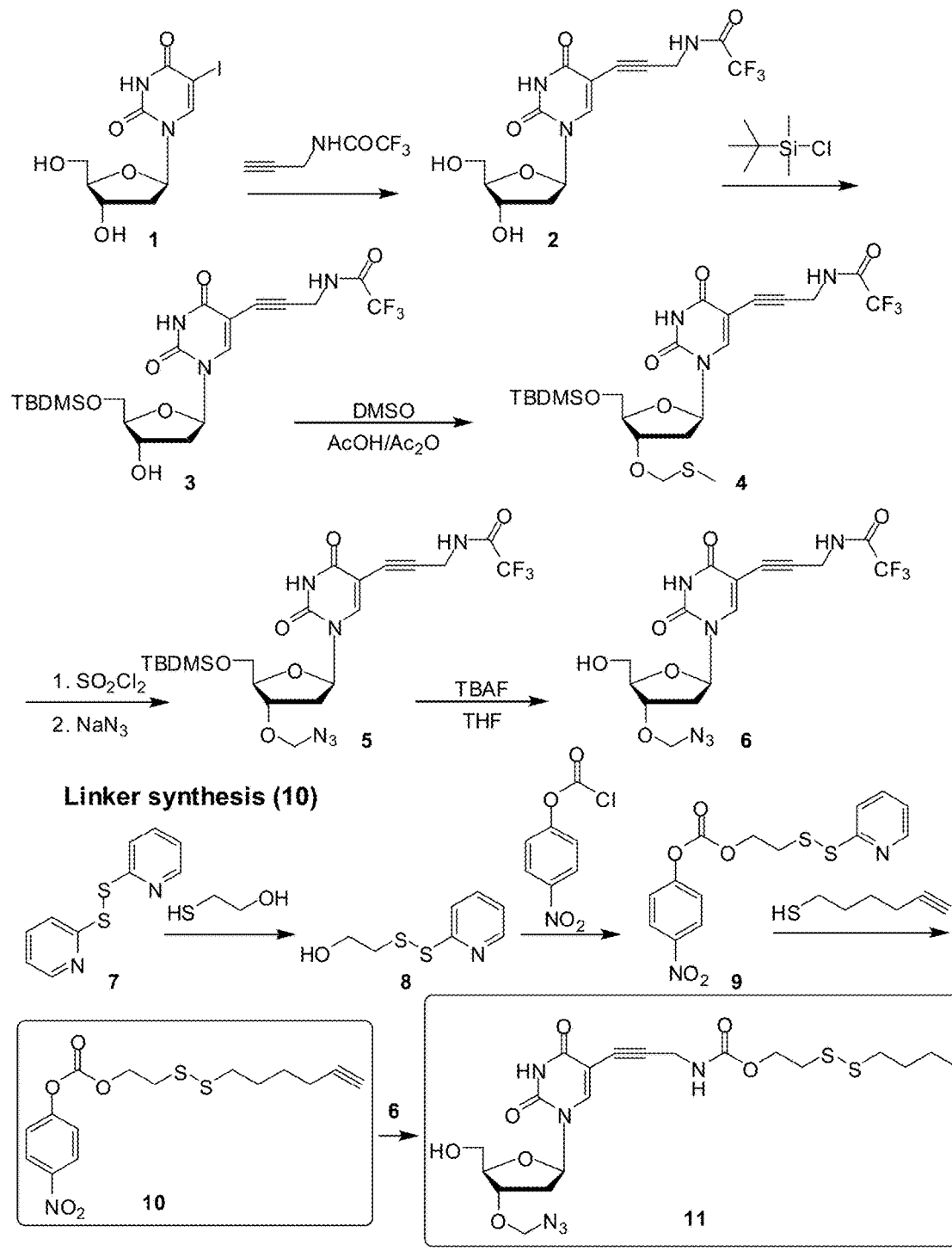
FIGS. 3A and 3B portrait the synthetic route for the preparation of a modified thymine/uridine deoxyribonucleotide to afford a reversible terminator with a BDP-FL-fluorophore attached, according to the present disclosure.
Figure 3B:
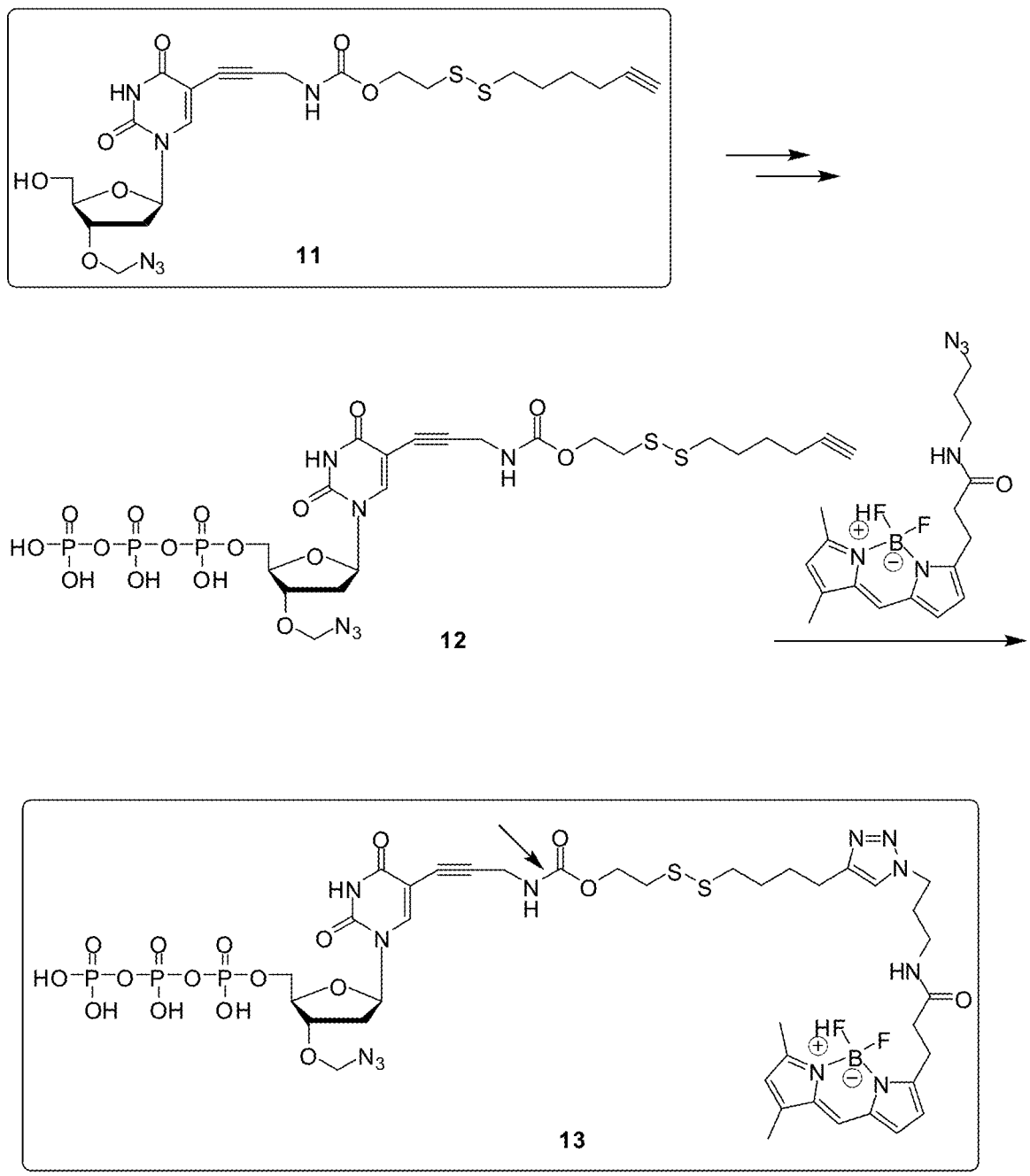

FIGS. 3A and 3B illustrate the synthesis of four exemplary 3'-O-azidomethyl modified labeled nucleotide triphosphates in which BDP-FL-fluorophore is attached to C-5 position of pyrimidines (C and U) or C-7 position of purine bases (A and G) through a disulfanylethoxycarbonylamino linkage (as shown in FIG. 2). Synthetic route for the preparation of a modified uridine nucleotide is depicted in FIGS. 3A and 3B. As shown in FIG. 3A (Scheme: Synthesis of New 3'-O-azidomethyl-5-dithio-linked terminators), silylation of the 5-propargyl-trifluoroacetamido uridine (2), prepared by palladium catalyzed coupling of 5-iodo-2'deoxyuridine (1) with N-trifluoroacetylpropargylamine afforded 5'-O-tert-butyldimethylsilyl-5-(3-trifluoroacetamidopropynyl)-2'-deoxyuridine (3). The 3'-hydroxy group in 3 is then converted to 3'-O-methoxymethyl sulfide using DMSO, acetic acid and acetic anhydride by Pummerer's rearrangement to afford intermediate 4. Intermediate 4 was further converted to the corresponding 3'-azidomethyl derivative 5 in a one-pot reaction, first by in-situ conversion to 3'-O-chloromethyl using sulfuryl chloride followed by an ensuing reaction with sodium azide. Removal of 5'-silyl group by tetrabutylammonium fluoride gave 3'-azidomethoxy-5-(3- aminopropynyl)-2'deoxyuridine (6). The linker 10 was synthesized via activated carbonate 9. Thus condensation of commercially available 2,2'-dithiodipyridine with 2-thiolethanol afforded intermediate 8. Intermediate 8 was further reacted with 4-nitrophenyl chlorocarbonate to afford pyridyl-disulfide carbonate 9. Activated carbonate linker 10, obtained from disulfide 9 and hex-5-yne-1-thiol, was finally condensed with 6, to afford the key intermediate 3'-azidomethyl-5-disulfide carbonate-2'-deoxyuridine 11.

Turning now to FIG. 3B. Triphosphorylation of 11 gives the triphosphate intermediate 12. A subsequent condensation of intermediate 12 with azido BDP-FL-fluorophore (commercially available from Lumiprobe Corporation, Hallandale Beach, Fla., USA) gave the desired fluorescently labeled triphosphate nucleotide terminator 13. Similarly to the strategies shown in FIGS. 3A and 3B, other azido fluorophore can be used to tag different dyes.

Other nucleotide terminators with deoxy-adenine, cytidine and guanine can be prepared using similar chemistry shown in FIGS. 3A and 3B to afford labeled nucleotide terminators as shown in FIG. 2.

A person skilled in the art would recognize that there are many different routes leading to the synthesis of a reversible terminator of the general formula (I):

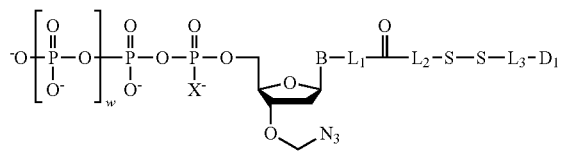

wherein w is 1-5; X is O, S, or $BH_3$; B is a nucleotide base or an analog thereof; $L_{1-3}$ are linkers; $D_1$ is a detectable label.

For example, the bond between $L_1$ and the carbonyl group can be formed from two respective intermediates; the bond between $L_2$ and the carbonyl group can be formed from two respective intermediates; the disulfide bond can be formed from two respective intermediates; and $L_3$ may be formed by joining two intermediates together through a bond-formation step. Each of $L_{1-3}$ may contain additional point of bond-making positions to connect two intermediates together in order to from the reversible terminator. Although the present disclosure only present a few synthetic routes leading to the reversible terminator, other similar or different synthetic routes are possible when taken into consideration of the particular structure of the targeted reversible terminator. Such synthetic methods to connect two intermediates are standard and commonly use published procedures which are well-known to those skilled in the art.

To prepare reversible terminators according to the present disclosure, the conversion of nucleosides to the corresponding nucleoside 5'-triphosphates may use any one of the many published protocols for carrying out this purpose. (See, for instance, Caton-Williams J, et al., "Use of a Novel 5'-Regioselective Phosphitylating Reagent for One-Pot Synthesis of Nucleoside 5'-Triphosphates from Unprotected Nucleosides," *Current Protocols in Nucleic Acid Chemistry*, 2013, 1.30.1-1.30.21; Nagata S, et al., "Improved method for the solid-phase synthesis of oligoribonucleotide 5'-triphosphates," *Chem. Pharm. Bull.*, 2012, 60(9):1212-15; Abramova et al., "A facile and effective synthesis of dinucleotide 5' triphosphates," *Bioorg. Med. Chem.*, 15:6549-6555, 2007; Abramova et al., "Synthesis of morpholine nucleoside triphosphates," *Tet. Lett.*, 45:4361, 2004; Lebedev et al., "Preparation of oligodeoxyribonucleotide 5'-triphosphates using solid support approach," *Nucleos. Nucleot. Nucleic. Acids*, 20: 1403, 2001; Hamel et al., "Synthesis of deoxyguanosine polyphosphates and their interactions with the guanosine 5'-triphosphate requiring protein synthetic enzymes of *Escherichia coli*," *Biochemistry*, 1975, 14(23): 5055-5060; Vaghefi M., "Chemical synthesis of nucleoside 5'-triphosphates," In: Nucleoside Triphosphates and their Analogs, pp. 1-22, Taylor & Francis, 2005; Burgess et al., "Synthesis of nucleoside triphosphates," *Chem. Rev.*, 100: 2047-2059, 2000).

Reversible terminators in the present disclosure comprise an azidomethyl group at the 3' oxygen of the sugar moiety. Reversible terminator nucleotides of this type are useful in methodologies for determining the sequence of polynucleotides. The methodologies in which these reversible terminator nucleotides are useful include, but are not limited to, automated Sanger sequencing, NGS methods including, but not limited to, sequencing by synthesis, and the like. Virtually any known method of analyzing or detecting a polynucleotide may optionally employ the presently disclosed reversible terminator nucleotides. Such methods may optionally employ a solid substrate to which the template is covalently bound. The solid substrate may be a particle or microparticle or flat, solid surface of the type used in current instrumentation for sequencing of nucleic acids. (See, for example, Ruparel et al., *Proc. Natl. Acad. Sci.*, 102:5932-5937, 2005; EP 1,974,057; WO 93/21340 and U.S. Pat. Nos. 5,302,509 and 5,547,839, and references cited therein). Optionally, the sequencing reaction employing the presently disclosed reversible terminator nucleotides may be performed in solution or the reaction is performed on a solid phase, such as a microarray or on a microbead, in which the DNA template is associated with a solid support. Solid supports may include, but are not limited to, plates, beads, microbeads, whiskers, fibers, combs, hybridization chips, membranes, single crystals, ceramics, and self-assembling monolayers and the like. Template polynucleic acids may be attached to the solid support by covalent binding such as by conjugation with a coupling agent or by non-covalent binding such as electrostatic interactions, hydrogen bonds or antibody-antigen coupling, or by combinations thereof. There are a wide variety of known methods of attaching nucleic acids to solid supports.

Linkers

Linkers or contemplated herein are of sufficient length and stability to allow efficient hydrolysis or removal by chemical or enzymatic means. Useful linkers will be readily available and may be capable of reacting with a hydroxyl moiety (or base or nucleophile) on one end of the linker or in the middle of the linker. One end of the linker may be capable of being bound to or modified by a label group, such as D1 or detectable label. The number of carbons or atom in a linker, optionally derivatized by other functional groups, must be of sufficient length to allow either chemical or enzymatic cleavage of the blocking group, if the linker is attached to a blocking group or if the linker is attached to the detectable label.

While precise distances or separation may be varied for different reaction systems to obtain optimal results, in many cases it will be desirable to provide a linkage that maintains the bulky label moiety at some distance away from the nucleotide, e.g., a linker of 1 to 20 nm in length, to reduce steric crowding in enzyme binding sites. Therefore, the length of the linker may be, for example, 1-50 atoms in length, or 1-40 atoms in length, or 2-35 atoms in length, or 3 to 30 atoms in length, or 5 to 25 atoms in length, or 10 to 20 atoms in length, etc.

Linkers may be comprised of any number of basic chemical starting blocks. For example, linkers may comprise linear or branched alkyl, alkenyl, or alkynyl chains, or combinations thereof, that provide a useful distance between the sugar group and the detectable label, for example, D1. For instance, amino-alkyl linkers, e.g., amino-hexyl linkers, have been used to provide label attachment to nucleotide analogs, and are generally sufficiently rigid to maintain such distances. The longest chain of such linkers may include as many as 2 atoms, 3 atoms, 4 atoms, 5 atoms, 6 atoms, 7 atoms, 8 atoms, 9 atoms, 10 atoms, or even 11-35 atoms, or even 35-50 atoms. The linear or branched linker may also contain heteroatoms other than carbon, including, but not limited to, oxygen, sulfur, phosphate, and nitrogen. A polyoxyethylene chain (also commonly referred to as polyethyleneglycol, or PEG) is a preferred linker constituent due to the hydrophilic properties associated with polyoxyethylene. Insertion of heteroatom such as nitrogen and oxygen into the linkers may affect the solubility and stability of the linkers.

The linker may be rigid in nature or flexible. Typically, rigid structures include laterally rigid chemical groups, e.g., ring structures such as aromatic compounds, multiple chemical bonds between adjacent groups, e.g., double or triple bonds, in order to prevent rotation of groups relative to each other, and the consequent flexibility that imparts to the overall linker. Thus, the degree of desired rigidity may be modified depending on the content of the linker, or the number of bonds between the individual atoms comprising the linker. Further, addition of ringed structures along the linker may impart rigidity. Ringed structures may include aromatic or non-aromatic rings. Rings may be anywhere from 3 carbons, to 4 carbons, to 5 carbons or even 6 carbons in size. Rings may also optionally include heteroatoms such as oxygen or nitrogen and also be aromatic or non-aromatic. Rings may additionally optionally be substituted by other alkyl groups and/or substituted alkyl groups.

Linkers that comprise ring or aromatic structures can include, for example aryl alkynes and aryl amides. Other examples of the linkers of the invention include oligopeptide linkers that also may optionally include ring structures within their structure.

For example, in some cases, polypeptide linkers may be employed that have helical or other rigid structures. Such polypeptides may be comprised of rigid monomers, which derive rigidity both from their primary structure, as well as from their helical secondary structures, or may be comprised of other amino acids or amino acid combinations or sequences that impart rigid secondary or tertiary structures, such as helices, fibrils, sheets, or the like. By way of example, polypeptide fragments of structured rigid proteins, such as fibrin, collagen, tubulin, and the like may be employed as rigid linker molecules.

All of the linkers which attach the detectable label to the base of the nucleotide comprise a disulfide moiety in the present disclosure. In addition, a second cleavable group such as a carbonate or a carbamate is placed in the vicinity of the disulfide bond between the disulfide bond and the base. The separation between the disulfide bond and the second cleavable group may be 2 or 3 atoms. In some embodiments, the separation may be an ethylene group, optionally with 1 or 2 substitutions. In other embodiments, the separation may be a propylene group, optionally with 1-3 substitutions.

Labels & Dyes

A label or detectable label, as in D1, of the present reversible terminators, may be any moiety that comprises one or more appropriate chemical substances or enzymes that directly or indirectly generate a detectable signal in a chemical, physical or enzymatic reaction. A large variety of labels are well known in the art. (See, for instance, PCT/GB2007/001770).

For instance, one class of such labels is fluorescent labels. Fluorescent labels have the advantage of coming in several different wavelengths (colors) allowing distinguishably labeling each different terminator molecule. (See, for example, Welch et al., *Chem. Eur. J.* 5(3):951-960, 1999). One example of such labels is dansyl-functionalized fluorescent moieties. Another example is the fluorescent cyanine-based labels Cy3 and Cy5, which can also be used in the present invention. (See, Zhu et al., *Cytometry,* 28:206-211, 1997). Labels suitable for use are also disclosed in Prober et al., *Science,* 238:336-341, 1987; Connell et al., *BioTechniques,* 5(4):342-384, 1987; Ansorge et al., *Nucl. Acids Res.,* 15(11):4593-4602, 1987; and Smith et al., *Nature,* 321:674, 1986. Other commercially available fluorescent labels include, but are not limited to, fluorescein and related derivatives such as isothiocyanate derivatives, e.g. FITC and TRITC, rhodamine, including TMR, texas red and Rox, bodipy, acridine, coumarin, pyrene, benzanthracene, the cyanins, succinimidyl esters such as NHS-fluorescein, maleimide activated fluorophores such as fluorescein-5-maleimide, phosphoramidite reagents containing protected fluorescein, boron-dipyrromethene (BODIPY) dyes, and other fluorophores, e.g. 6-FAM phosphoramidite 2. All of these types of fluorescent labels may be used in combination, in mixtures and in groups, as desired and depending on the application.

Various commercially available fluorescent labels are known in the art, such as Alexa Fluor Dyes, e.g., Alexa 488, 555, 568, 660, 532, 647, and 700 (Invitrogen-Life Technologies, Inc., California, USA, available in a wide variety of wavelengths, see for instance, Panchuk, et al., *J. Hist. Cyto.,* 47:1179-1188, 1999). Also commercially available are a large group of fluorescent labels called ATTO dyes (available from ATTO-TEC GmbH in Siegen, Germany). These fluorescent labels may be used in combinations or mixtures to provide distinguishable emission patterns for all terminator molecules used in the assay since so many different absorbance and emission spectra are commercially available.

In various exemplary embodiments, a label comprises a fluorescent dye, such as, but not limited to, a rhodamine dye, e.g., R6G, R1 10, TAMRA, and ROX, a fluorescein dye, e.g., JOE, VIC, TET, HEX, FAM, etc., a halo-fluorescein dye, a cyanine dye. e.g., CY3, CY3.5, CY5, CY5.5, etc., a BODIPY® dye, e.g., FL, 530/550, TR, TMR, etc., a dichlororhodamine dye, an energy transfer dye, e.g., BIGD YE™ v 1 dyes, BIGD YE™ v 2 dyes, BIGD YE™ v 3 dyes, etc., Lucifer dyes, e.g., Lucifer yellow, etc., CASCADE BLUE®, Oregon Green, and the like. Other exemplary dyes are provided in Haugland, Molecular Probes Handbook of Fluorescent Probes and Research Products, Ninth Ed. (2003) and the updates thereto. Non-limiting exemplary labels also include, e.g., biotin, weakly fluorescent labels (see, for instance, Yin et al., *Appl Environ Microbiol.,* 69(7):3938, 2003; Babendure et al., *Anal. Biochem.,* 317(1):1, 2003; and Jankowiak et al., *Chem. Res. Toxicol.,* 16(3):304, 2003), non-fluorescent labels, colorimetric labels, chemiluminescent labels (see, Wilson et al., Analyst, 128(5):480, 2003; Roda et al., *Luminescence,* 18(2): 72, 2003), Raman labels, electrochemical labels, bioluminescent labels (Kitayama et al., *Photochem. Photobiol.*, 77(3):333, 2003; Arakawa et al., *Anal. Biochem.*, 314(2):206, 2003; and Maeda, *J. Pharm. Biomed. Anal.*, 30(6): 1725, 2003), and the like.

Multiple labels can also be used in the invention. For example, bi-fluorophore FRET cassettes (*Tet. Letts.*, 46:8867-8871, 2000) are well known in the art and can be utilized in the disclosed methods. Multi-fluor dendrimeric systems (*J. Amer. Chem. Soc.*, 123:8101-8108, 2001) can also be used. Other forms of detectable labels are also available. For example, microparticles, including quantum dots (Empodocles, et al., *Nature*, 399:126-130, 1999), gold nanoparticles (Reichert et al., *Anal. Chem.*, 72:6025-6029, 2000), microbeads (Lacoste et al., *Proc. Natl. Acad. Sci. USA*, 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Thus, a "label" as presently defined is a moiety that facilitates detection of a molecule. Common labels in the context of the present invention include fluorescent, luminescent, light-scattering, and/or colorimetric labels. Suitable labels may also include radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. As other non-limiting examples, the label can be a luminescent label, a light-scattering label (e.g., colloidal gold particles), or an enzyme (e.g., Horse Radish Peroxidase (HRP)).

Fluorescence energy transfer (FRET) dyes may also be employed, such as DY-630/DY-675 from Dyomics GmbH of Germany, which also commercially supplies many different types of dyes including enzyme-based labels, fluorescent labels, etc. (See, for instance, Dohm et al., "Substantial biases in ultra-short read data sets from high-throughput DNA sequencing," *Nucleic Acids Res.*, 36:e105, 2008). Other donor/acceptor FRET labels include, but are not limited to:

| Donor | Acceptor | $R_0$ (Å) |
|---|---|---|
| Fluorescein | Tetramethylrhodamine | 55 |
| IAEDANS | Fluorescein | 46 |
| EDANS | Dabcyl | 33 |
| Fluorescein | Fluorescein | 44 |
| BODIPY FL | BODIPY FL | 57 |
| Fluorescein | QSY 7 and QSY 9 dyes | 61 |

(See also, Johansen, M. K., "Choosing Reporter-Quencher Pairs for Efficient Quenching Through Formation of Intramolecular Dimers," Methods in Molecular Biology, vol. 335: Fluorescent Energy Transfer Nucleic Acid Probes: Designs and Protocols, Edited by: V. V. Didenko, Humana Press Inc., Totowa, N.J.). Other dye quenchers are commercially available, including dabcyl, QSY quenchers and the like. (See also, Black Hole Quencher Dyes from Biosearch Technologies, Inc., Novato, Calif.; Iowa Black Dark Quenchers from Integrated DNA Technologies, Inc. of Coralville, Iowa; and other dye quenchers sold by Santa Cruz Biotechnology, Inc. of Dallas, Tex.).

The label and linker construct can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

Polymerase Enzymes Used in SBS/SBE Sequencing

As already commented upon, one of the key challenges facing SBS or SBE technology is finding reversible terminator molecules capable of being incorporated by polymerase enzymes efficiently and which provide a blocking group that can be removed readily after incorporation. Thus, to achieve the presently claimed methods, polymerase enzymes must be selected which are tolerant of modifications at the 3' and 5' ends of the sugar moiety of the nucleoside analog molecule. Such tolerant polymerases are known and commercially available.

Preferred polymerases lack 3'-exonuclease or other editing activities. As reported elsewhere, mutant forms of 9° N-7(exo-) DNA polymerase can further improve tolerance for such modifications (WO 2005024010; WO 2006120433), while maintaining high activity and specificity. An example of a suitable polymerase is THERMINATOR™ DNA polymerase (New England Biolabs, Inc., Ipswich, Mass.), a Family B DNA polymerase, derived from *Thermococcus* species 9° N-7. The 9° N-7(exo-) DNA polymerase contains the D141A and E143A variants causing 3'-5' exonuclease deficiency. (See, Southworth et al., "Cloning of thermostable DNA polymerase from hyperthermophilic marine Archaea with emphasis on *Thermococcus* species 9° N-7 and mutations affecting 3'-5' exonuclease activity," *Proc. Nat. Acad. Sci. USA*, 93(11): 5281-5285, 1996). THERMINATOR™ I DNA polymerase is 9° N-7 (exo-) that also contains the A485L variant. (See, Gardner et al., "Acyclic and dideoxy terminator preferences denote divergent sugar recognition by archaeon and Taq DNA polymerases," *Nucl. Acids Res.*, 30:605-613, 2002). THERMINATOR™ III DNA polymerase is a 9° N-7(exo-) enzyme that also holds the L408S, Y409A and P410V mutations. These latter variants exhibit improved tolerance for nucleotides that are modified on the base and 3' position. Another polymerase enzyme useful in the present methods and kits is the exo-mutant of KOD DNA polymerase, a recombinant form of *Thermococcus kodakaraensis* KOD1 DNA polymerase. (See, Nishioka et al., "Long and accurate PCR with a mixture of KOD DNA polymerase and its exonuclease deficient mutant enzyme," *J. Biotech.*, 88:141-149, 2001). The thermostable KOD polymerase is capable of amplifying target DNA up to 6 kbp with high accuracy and yield. (See, Takagi et al., "Characterization of DNA polymerase from *Pyrococcus* sp. strain KOD1 and its application to PCR," *App. Env. Microbiol.*, 63(11):4504-4510, 1997). Others are Vent (exo-), Tth Polymerase (exo-), and Pyrophage (exo-) (available from Lucigen Corp., Middletown, Wis., US). Another non-limiting exemplary DNA polymerase is the enhanced DNA polymerase, or EDP. (See, WO 2005/024010).

When sequencing using SBE, suitable DNA polymerases include, but are not limited to, the Klenow fragment of DNA polymerase I, SEQUENASE™ 1.0 and SEQUENASE™ 2.0 (U.S. Biochemical), T5 DNA polymerase, Phi29 DNA polymerase, THERMOSEQUENASE™ (Taq polymerase with the Tabor-Richardson mutation, see Tabor et al., *Proc. Natl. Acad. Sci. USA*, 92:6339-6343, 1995) and others known in the art or described herein. Modified versions of these polymerases that have improved ability to incorporate a nucleotide analog of the invention can also be used.

Further, it has been reported that altering the reaction conditions of polymerase enzymes can impact their promiscuity, allowing incorporation of modified bases and reversible terminator molecules. For instance, it has been reported that addition of specific metal ions, e.g., $Mn^{2+}$, to polymerase reaction buffers yield improved tolerance for modified nucleotides, although at some cost to specificity (error rate). Additional alterations in reactions may include conducting the reactions at higher or lower temperature, higher or lower pH, higher or lower ionic strength, inclusion of co-solvents or polymers in the reaction, and the like.

Random or directed mutagenesis may also be used to generate libraries of mutant polymerases derived from native species; and the libraries can be screened to select mutants with optimal characteristics, such as improved efficiency, specificity and stability, pH and temperature optimums, etc. Polymerases useful in sequencing methods are typically polymerase enzymes derived from natural sources. Polymerase enzymes can be modified to alter their specificity for modified nucleotides as described, for example, in WO 01/23411, U.S. Pat. No. 5,939,292, and WO 05/024010. Furthermore, polymerases need not be derived from biological systems.

De-Blocking: Removal of the 3' Blocking group and the Detectable Label

After incorporation, both the 3' blocking group (azidomethyl group) and the detectable label attached to the base group of the nucleotide via a disulfide can be removed from the reversible terminator molecules by various means including, but not limited to, chemical means. Removal of the blocking group reactivates or releases the growing polynucleotide strand, freeing it to be available for subsequent extension by the polymerase enzyme. This enables the controlled extension of the primers by a single nucleotide in a sequential manner. The reversible terminators disclosed herein are specially designed to allow such removal by chemical means, which is sometimes preferred, as opposed to enzymatic means.

In one embodiment, the chemical reagents to carry out the be-blocking reaction are trialkylphosphine and triarylphosphine. In another embodiment, the chemical reagent to carry out the be-blocking reaction is trialkylphosphine. In still another embodiment, the chemical reagent to carry out the be-blocking reaction is tris(2-carboxyethyl)phosphine.

Trialkylphosphine can reduce azides to the corresponding amines in the presence of water, which is known as the Staudinger reaction. The phosphine acts as an oxygen acceptor from the water while the hydrogen atoms from the water add to the azide to form the amine products and eliminate nitrogen gas as the by-product. In general, trialkylphosphine is more effective than triarylphosphine to reduce the azide to amine.

Similarly, trialkylphosphines reduce organic disulfides to thiols in water. Again, the strength of the phosphorus-oxygen bond renders the reduction irreversible. Since trialkylphosphines are kinetically stable in aqueous solution, selective for the reduction of the disulfide linkage, and unreactive toward many other functional groups (other than disulfides or azides), they are attractive reducing agents in biochemical applications, including reactions with nucleotides such as DNA and RNA molecules.

One advantage to use trialkylphosphines over triarylphosphines (e.g., $Ph_3P$) is that the former are more likely to be liquids, which can be more easily kept from exposing to air. Another advantage of using trialkylphosphines is the fact that the resulting trialkylphosphine oxide can be water soluble and thus, are readily removed from the water-insoluble products by a simple wash with aqueous solutions.

Definitions

All terms are intended to be understood as they would be understood by a person skilled in the art. Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "hydroxyl protective group" is intended to include any group which forms a derivative of the hydroxyl group that is stable to the projected reactions wherein said hydroxyl protective group subsequently optionally can be selectively removed. Said hydroxyl derivative can be obtained by selective reaction of a hydroxyl protecting agent with a hydroxyl group.

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

A "linker group" maybe a cleavable linker as described in this disclosure or a group selected from alkylene, alkenylene, alkynylene, heteroalkylene, cycloalkylene, heteroarylalkylene, heterocyclylalkylene, arylene, heteroarylene, or $[R_2—K—R_2]_n$, and each linker group may be substituted with 0-6 $R_5$; each $R_2$ is independently alkylene, alkenylene, alkynylene, heteroarylalkylene, cycloalkylene, heterocycloalkylene, arylene, or heteroarylalkylene; K is none, —O—, —S—, —S(O)—, —S(O$_2$)—, —C(O)—, —C(O)O—, —C(O)N(R$_3$)—, or

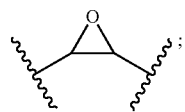 [SMILES: *C1OC1*]

R$_3$ is hydrogen, alkyl, alkenyl, alkynyl, arylalkyl, heteroalkyl, cycloalkyl, heterocycloalkyl, cycloalkylalkyl, cycloaryl, or heterocycloaryl, substituted with 0-6 R$_5$; R$_5$ is halogen, alkyl, —OR$_6$, —N(R$_6$)$_2$, —SR$_6$, —S(O)R$_6$, —SO$_2$R$_6$, or —C(O)OR$_6$; each R$_6$ is independently —H, alkyl, alkenyl, alkynyl, arylalkyl, cycloalkylalkyl, or heterocycloalkyl; and n is an integer from 1-4;

A "sugar moiety" encompasses both ribose and deoxyribose and their derivatives/analogs.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The term "polynucleotide" (and the equivalent term "nucleic acid") encompasses any physical string of monomer units that can be corresponded to a string of nucleotides, including a polymer of nucleotides, e.g., a typical DNA or RNA polymer, peptide nucleic acids (PNAs), modified oligonucleotides, e.g., oligonucleotides comprising nucleotides that are not typical to biological RNA or DNA, such as 2'-O-methylated oligonucleotides, and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

The term "analog" in the context of nucleic acid analog is meant to denote any of a number of known nucleic acid analogs such as, but not limited to, LNA, PNA, etc. Further, a "nucleoside triphosphate analog" may contain 3-7 phosphate groups, wherein one of the oxygen (—O$^-$) on the phosphate may be replaced with sulfur (—S$^-$) or borane (—BH$_3^-$). Still further, a "nucleoside triphosphate analog" may contain a base which is an analog of adenine (A), guanine (G), thymine (T), cytosine (C) and uracil (U). For example, the bases are included:

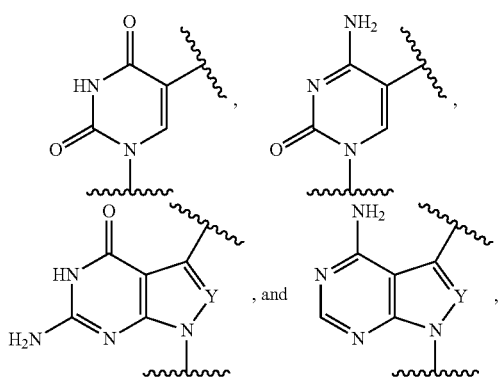

wherein Y is CH or N.

The term "aromatic" used in the present application means an aromatic group which has at least one ring having a conjugated pi electron system, i.e., aromatic carbon molecules having 4n+2 delocalized electrons, according to Huckel's rule, and includes both carbocyclic aryl, e.g., phenyl, and heterocyclic aryl groups, e.g., pyridine. The term includes monocyclic or fused-ring polycyclic, i.e., rings which share adjacent pairs of carbon atoms, groups.

The term "heterocyclic nucleic acid base" used herein means the nitrogenous bases of DNA or RNA. These bases can be divided into two classes: purines and pyrimidines. The former includes guanine and adenine and the latter includes cytosine, thymine, and uracil.

The term "aromatic" when used in the context of "aromatic solvent" as used in the present disclosure means any of the known and/or commercially available aromatic solvents, such as, but not limited to, toluene, benzene, xylenes, any of the Kesols, and/or GaroSOLs, and derivatives and mixtures thereof.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated, i.e. $C_1$-$C_{10}$ means one to ten carbon atoms in a chain. Non-limiting examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N ($CH_3$)—$CH_3$, —$CH_2$—S—$CH_2$—$CH_3$, —$CH_2$—$CH_2$—S(O)—$CH_2$, —$CH_2$—$CH_2$—S(O)$_2$—$CH_3$, —CHCH—O—$CH_3$, —Si($CH_3$)$_3$, —$CH_2$—CHN—O$CH_3$, and —CHCH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini, e.g., alkyleneoxy, alkylenedioxy, alkyleneamino, alkylenediamino, and the like. Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring, such as those that follow Hückel's rule (4n+2, where n is any integer), or multiple rings (preferably from 1 to 5 rings), which are fused together or linked covalently and including those which obey Clar's Rule. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms, e.g., aryloxy, arylthioxy, arylalkyl, includes both aryl and heteroaryl rings as defined above. Thus, the term "arylalkyl" is meant to include those radicals in which an aryl group is attached to an alkyl group, e.g., benzyl, phenethyl, pyridylmethyl and the like, including those alkyl groups in which a carbon atom, e.g., a methylene group, has been replaced by, for example, an oxygen atom, e.g., phenoxymethyl, 2-pyridyloxymethyl, 3-(1-naphthyloxy)propyl, and the like.

Each of the above terms, e.g., "alkyl," "heteroalkyl," "aryl" and "heteroaryl," is meant to include both substituted and unsubstituted forms of the indicated radical. Preferred substituents for each type of radical are provided below.

Substituents for the alkyl and heteroalkyl radicals, including those groups often referred to as alkylene, alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: —OR', =O, =NR', =N—OR", —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR"R", —NRSO$_2$R', —CN and —NO$_2$ in a number ranging from zero to (2M'+1), where M' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl, e.g., —CF$_3$ and —CH$_2$CF$_3$) and acyl, e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', —NR'R", —SR', -halogen, SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR''', —NR—C(NR'R")=NR''', —S(O)R', —S(O)$_2$R', —S(O)$_2$NR"R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

Unless otherwise noted, the term "catalytic amount," as used herein, includes that amount of the reactant that is sufficient for a reaction of the process of the invention to occur. Accordingly, the quantity that constitutes a catalytic amount is any quantity that serves to allow or to increase the rate of reaction, with larger quantities typically providing a greater increase. The quantity used in any particular application will be determined in large part by the individual needs of the manufacturing facility. Factors which enter into such a determination include the catalyst cost, recovery costs, desired reaction time, and system capacity. It will be most convenient to use an amount of reactant in the range from about 0.001 to about 0.5 equivalents, from about 0.001 to about 0.25 equivalents, from about 0.01 to about 0.25 equivalents, from about 0.001 to about 0.1, from about 0.01 to about 0.1 equivalents, including about 0.005, about 0.05 or about 0.08 equivalents of the reactant/substrate, or in the range from about 0.001 to about 1 equivalents, from about 0.001 to about 0.5 equivalents, from about 0.001 to about 0.25 equivalents, from about 0.001 to about 0.1 equivalents, from about 0.01 to about 0.5 equivalents or from about 0.05 to about 0.1 equivalents, including about 0.005, about 0.02 or about 0.04 equivalents.

Unless otherwise noted, the term "cleavable chemical group," as used herein, includes chemical group that caps the —OH group at the 3'-position of the ribose or deoxyribose in the nucleotide analogue is any chemical group that could be used as long as the group 1) is stable during the polymerase reaction, 2) does not interfere with the recognition of the nucleotide analogue by polymerase as a substrate, 3) is cleavable, and 4) cleavable by the same chemical reagent which cleaves the disulfide bond between the detectable label and the base.

Applicants are aware that there are many conventions and systems by which organic compounds may be named and otherwise described, including common names as well as systems, such as the IUPAC system.

Abbreviations

Abbreviations used throughout the present application have the meanings provided below. The meanings provided below are not meant to be limiting, but are meant to also encompass any equivalent common or systematic names understood by one of skill in the art. The meaning commonly understood by one of skill in the art should be ascribed to any other abbreviated names not listed below.

$I_2$=iodine
TBDMS=tert-butyldimethylsilyl
TBDPS=tert-butyldiphenylsilyl
BOC=tert-Butyloxycarbonyl
Pyr=pyridine base
THF=tetrahydrofuran
TsOH=p-toluene sulfonic acid
DCA=dichloroacetic acid
$Bu_3N$=tributyl amine
DMF=dimethylformamide
Py=pyridine
TEAB=triethylammonium bicarbonate
DMTO=4,4'-dimethoxytriphenylmethoxy
CEO=2-cyanoethoxy
TIPSCl=triisopropylsilyl ether chloride
Et=ethyl
Ph=phenyl
$(PhO)_2P(O)Cl$=diphenylphosphoryl chloride
CEO-$P(NiPr_2)_2$=O-(2-cyanoethyl)-N,N,N,N-tetraisopropylphosphorodiamidite
$iPr_2NH$=diisopropylamine
DBU=1,8-diazabicycloundec-7-ene
FMOC=fluorenylmethyl oxycarbonyl
TCEP=(tris(2-carboxyethyl)phosphine)
CDI=1,1'-carbonyldiimidazole
MeOH=methanol
TBA=tert-butyl alcohol or 2-methyl-2-propanol
TEA=triethanolamine
TFP=tetrafluoropropanol or 2,2,3,3-tetrafluoro-1-propanol
BSA=bovine serum albumin
DTT=dithiothreitol
ACN=acetonitrile
NaOH=sodium hydroxide
IE HPLC=ion-exchange high performance liquid chromatography
TLC=thin-layer chromatography
TCEP=tris(2-carboxyethyl)phosphine Synthetic Methods The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

For instance, in all instances, where a drying agent is used, contemplated drying agents include all those reported in the literature and known to one of skill, such as, but not limited to, magnesium sulfate, sodium sulfate, calcium sulfate, calcium chloride, potassium chloride, potassium hydroxide, sulfuric acid, quicklime, phosphorous pentoxide, potassium carbonate, sodium, silica gel, aluminum oxide, calcium hydride, lithium aluminum hydride (LAH), potassium hydroxide, and the like. (See, Burfield et al., "Dessicant Efficiency in Solvent Drying. A Reappraisal by Application of a Novel Method for Solvent Water Assay," *J. Org. Chem.*, 42(18):3060-3065, 1977). The amount of drying agent to add in each work up may be optimized by one of skill in the art and is not particularly limited. Further, although general guidance is provided for work-up of the intermediates in each step, it is generally understood by one of skill that other optional solvents and reagents may be equally substituted during the work-up steps. However, in some exceptional instances, it was found the very specific work-up conditions are required to maintain an unstable intermediate. Those instances are indicated below in the steps in which they occur.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6$^{th}$ Ed., University Science Books, Sausalito, Calif., 1998, Ann B. McGuire, Ed., pp. 45-59). Though certain organic co-solvents and quenching agents may be indicated in the steps described below, other equivalent organic solvents and quenching agents known to one of skill may be employed equally as well and are fully contemplated herein. Further, most of the work-ups in most steps may be further altered according to preference and desired end use or end product. Drying and evaporation, routine steps at the organic synthetic chemist bench, need not be employed and may be considered in all steps to be optional. The number of extractions with organic solvent may be as many as one, two, three, four, five, or ten or more, depending on the desired result and scale of reaction. Except where specifically noted, the volume, amount of quenching agent, and volume of organic solvents used in the work-up may be varied depending on specific reaction conditions and optimized to yield the best results.

Additionally, where inert gas or noble gas is indicated, any inert gas commonly used in the art may be substituted for the indicated inert gas, such as argon, nitrogen, helium, neon, etc.

A number of patents and publications are cited herein in order to more fully describe and disclose the present methods, compounds, compositions and kits, and the state of the art to which they pertain. The references, publications, patents, books, manuals and other materials cited herein to illuminate the background, known methods, and in particular, to provide additional details with respect to the practice of the present methods, compositions and/or kits, are all incorporated herein by reference in their entirety for all purposes, to the same extent as if each individual reference was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

It is understood that the examples and embodiments described herein are for illustrative purposes and that various modifications or changes in light thereof will be suggested to persons skilled in the art and are to be included within the spirit and purview of this application and scope of the claims. Accordingly, the following examples are offered to illustrate, but not to limit, the claimed invention.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The following examples describe the detail synthetic steps shown in FIGS. 4-11.

Example 1

Synthesis of 3'-O-azidomethyl-5-(Fluorescein-dithiolinker-cabamate)-2'-deoxyuridinetriphosphate (33)

Figure 4:
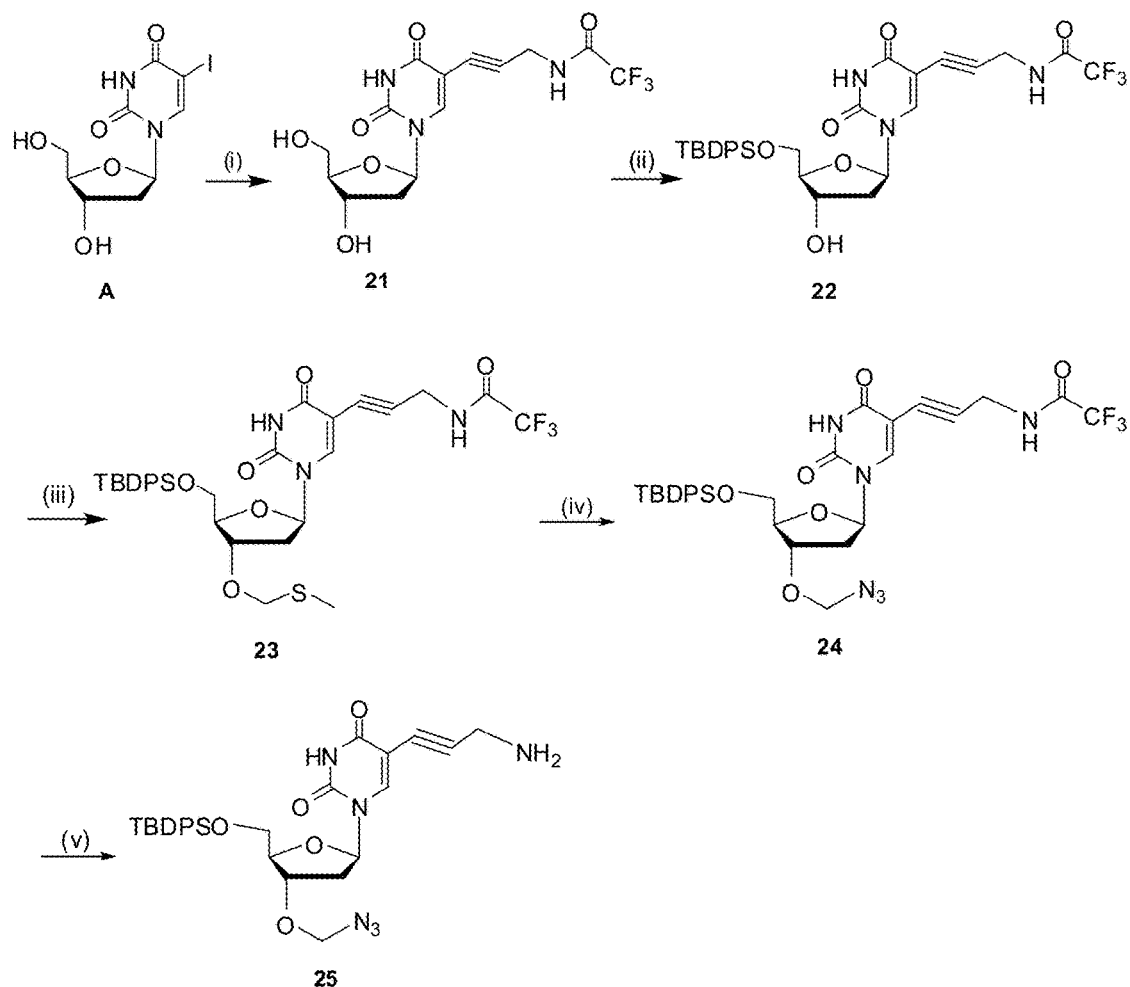
FIGS. 4, 5, and 6 depict the synthetic route for the preparation of a reversible terminator with a fluorescein as its fluorophore, according to the present disclosure.
Figure 5:
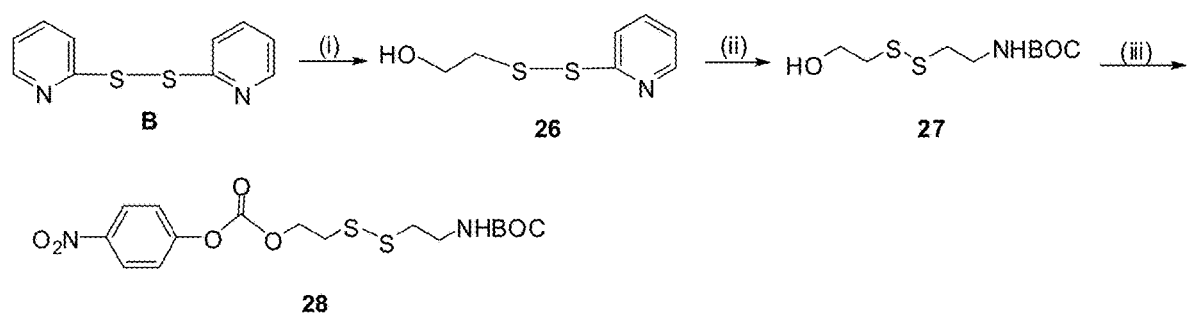
Figure 6:
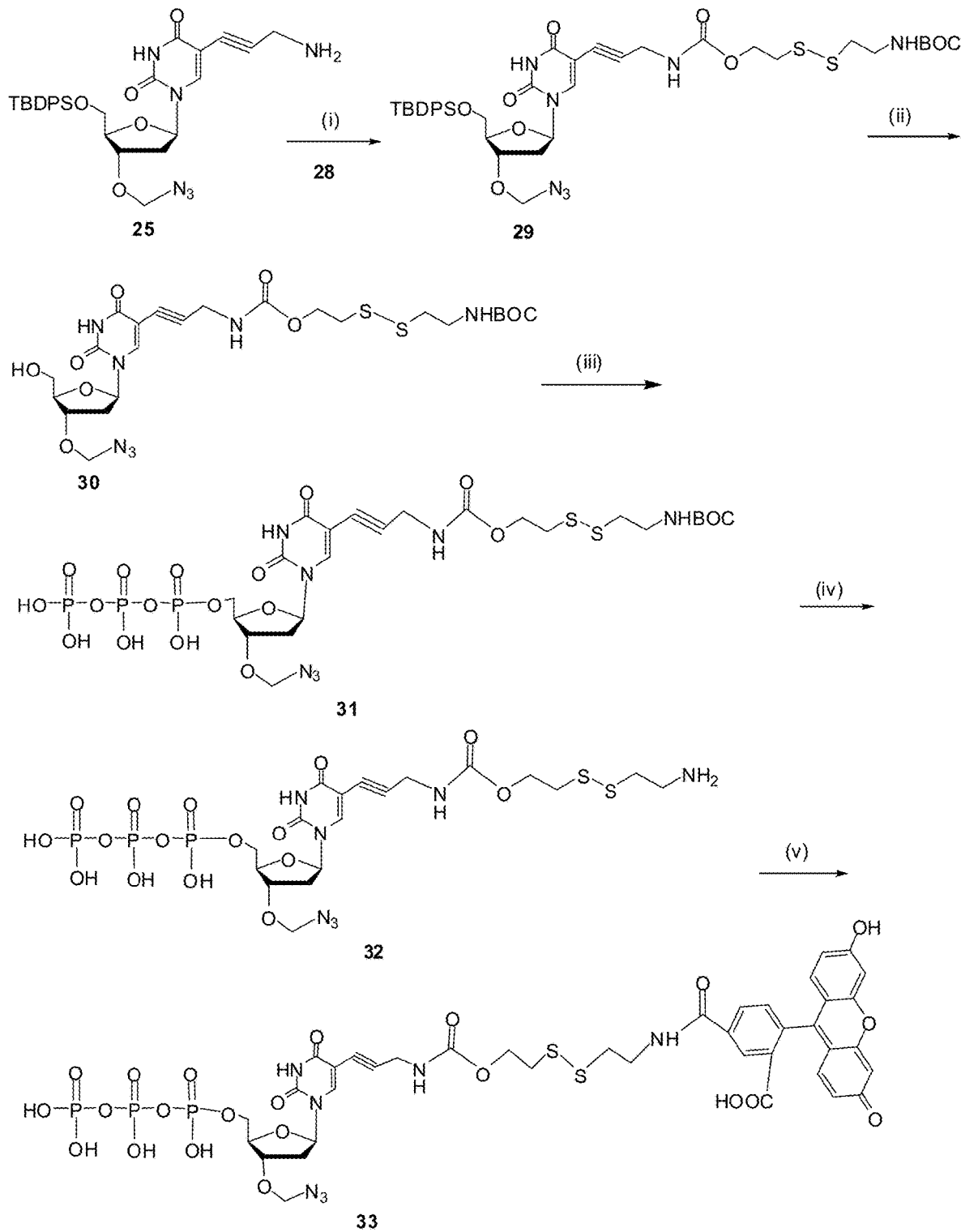

The title compound was prepared according the methods shown in FIGS. 4-6. Specifically, reagents and conditions used in FIG. 4 are: (i). trifluoro-N-prop-2-ynyl-acetamide, Pd(PPh$_3$)$_4$, CuI, triethylamine, DMF, RT, 12 h; (ii). tert-butyldiphenylsilylchloride, pyridine, RT, 6 h; (iii). DMSO, AcOH, Ac$_2$O, RT, 12 h; (iv). a) SOCl$_2$, 0° C., 1 h; b) NaN$_3$, DMF, 4 h; (v) NH$_4$OH, MeOH, 55° C., 3 h.; reagents and conditions used in FIG. 5 are: (i) 2-mercaptoethanol, pyridine, anhydrous MeOH, RT, 12 h, (ii) BOC-cysteamine, pyridine, MeOH, RT, 12 h, (iii) 4-nitrophenylchloroformate, Et$_3$N, MeCN; and reagents and conditions used in FIG. 6 are: (i) 28, NaHCO$_3$/Na$_2$CO$_3$ buffer (pH 9.2), acetonitrile, (ii) Et$_3$N.3HF, THF, 55 C, 4 h, (iii) (a) 2-chloro-1H-1,3,2-benzodioxaphosphorin-4-one, pyridine, THF, 1.5 h, (b). tributylamine, tributylammonium pyrophosphate, 4 h; (c) tert-butylhydogenperoxide, 1 h, (iv) aqueous TFA, (v). 5-Fluroscein-NHS ester, NaHCO$_3$/Na$_2$CO$_3$ buffer (pH 9.2).

Synthesis of 5-[3-(2,2,2,-trifluoroacetamido)-prop-1-ynyl]-2'deoxyuridine (21). To a solution of 5-iodouridine A (5.0 g, 14.1 mmol) in anhyd. DMF (40 mL), CuI (0.20 g. 1.05 mmol) and Pd(PPh$_3$)$_4$ (0.41 g, 0.035 mmol) were added under nitrogen. After stirring for 10 min. triethylamine (4.0 mL 28.6 mmol) and trifluoro-N-prop-2-ynyl-acetamide (5.4 g, 35.7 mmol) were added and the reaction mixture was stirred overnight at room temperature. All the volatiles were removed under vacuum and the residue was purified by flash chromatography on silica gel [EtOAc/MeOH (0-15%)] to afford the desired product as yellow solid 4.1 g (76%). 1H-NMR (DMSO-d6) δ11.68, (br s, 1H, NH), 10.02 (s, 1H, NH), 7.94 (s, 7.94 (s, 1H, H6), 6.11 (t, J=7.2 Hz, H-1'), 5.29 (d, J=0.4 Hz, 1H, OH), 4.21 (m, 3H, H-3', NCH$_2$), 3.71-3.83 (m, 2H, CH2-5'), 2.15-2.19 (m, 1H, H-2'), 2.03-2.08 (m, 1H, H-2'), Mass, Calcd for C$_{14}$H$_{14}$F$_3$N$_3$O$_6$ (M+Na), 400, Found 400.

Synthesis of 5'-O-tert-butyldiphenylsilyl-5-[3(2,2,2,-trifluoroacetamido-prop-1ynyl]-2'deoxyuridine (22). To a cooled (0° C.) solution of 21 (2.5 g, 6.61 mmol) in anhydrous pyridine (50 mL), tert-butyldiphenylsilyl chloride (2.1 g, 7.63 mmol) was added slowly under $N_2$ and the reaction mixture was further stirred at room temp overnight at room temp. The volatiles were removed under vacuum and the residue was purified by flash chromatography on silica gel (EA in hexanes from 75% to 100%) to afford desired product as white solid (2.82 g, 71%). 1H-NMR (DMSO-d6) δ 11.71 (br S, 1H, NH), 9.98 (s, 1H, NH), 8.60 (s, 1H, NH), 8.14 (s, 1H, H-6), 7.62-7.65 (m, 4H, Ar-H), 6.12 (t, J=6.9 Hz, HC-1'), 5.32 (d=4.4 Hz, OH), 4.23-4.27 (m, 1H, HC-3'), 4.09 (d, J=4.8 Hz, $NCH_2$), 3.83-3.88 (m, 1H, CH2-5'), 3.68-3.74 (m, 1H, H-5'), 2.18 (m, 2H, H-5'), 1.00 (s, 9H, $CH_3x3$); Mass, Calcd for $C_{30}H_{32}F_3N_3O_6Si$ (M+Na), 638.6 found 638.

Synthesis of 5'-O-tert-butyldiphenylsilyl-3'-O-methylthiomethyl-5-[3(2,2,2,-trifluoroacetamido-prop-1-ynyl]-2'deoxyuridine (23). To a solution of 22 (2.0 g, 3.24 mmol) in DMSO (5.2 mL), acetic acid (1.1 mL) and acetic anhydride (3.5 mL) were added subsequently under $N_2$ and reaction was stirred overnight at room temperature. The reaction mixture was concentrated under vacuum and the residue was diluted with EA and poured in saturated $NaHCO_3$ solution (150 mL) and stirred for 1 h. The aqueous layer was extracted with EA. The combined org layer was dried ($MgSO_4$), filtered and concentrated to afford an oil. The residue was purified by flash column chromatography over silica gel and the desired product was eluted with 40-80% EA in hexanes as white solid (1.22 g, 55%). 1H-NMR (DMSO-d6) δ 8.60 (br s, 1H, NH), 8.17 (s, 1H, H-6), 7.68-7.71 (m, 4H, Ar-H), 7.41-7.50 (m, 6H, Ar-H), 6.30 (dd, J=5.6 Hz, and 2.8 Hz, 1H, H-1'), 4.6-4.64 2H, $OCH_2S$), 4.13-4.15 (m-H-3'), 4.06-4.08 (m, 3H, H-3' and $NCH_2$), 3.98-4.02 (m, 1H, H-5'), 3.79-3.82 (m, 1H-H-5'), 2.54-2.59 (m, 1H, H-2'), 2.44-2.48 (M, 1HH-2'), Mass calc for $C_{32}H_{36}F_3N_3O_6SSi$, 675.8, Found (M+H), 676.

Synthesis of 5'-O-tert-butyldiphenylsilyl-3'-O-azidomethyl-5-[3(2,2,2,-trifluoroacetamido-prop-1-ynyl]-2'deoxyuridine (24). A solution of 23 (2.5 g, 3.70 mmol) and cyclohexene (3.8 mL, 37.5 mmol in anhydrous dichloromethane was cooled to 0° C., and sulfurylchloride (1M solution in DCM, 18.5 mL, 18.5 mmol) was added to it drop wise under $N_2$. After stirring for 1 h, TLC didn't show any starting material. Volatiles were removed under vacuum and the residue was dissolved in anhyd DMF and sodium azide (1.45 g, 37.5 mmol) was added to it and stirred further for 3 h. The reaction was quenched with dichloromethane and organic layer washed with satd. aq. brine solution. The organic layer was dried over anhyd. $MgSO_4$ and concentrated under vacuum. The residue was chromatographed over silica gel and the desired product was eluted with 40-60% EA in Hexanes as white solid (1.05 g, 42%). 1H-NMR (CDCl$_3$) δ 8.93 (br s, 1H, NH), 8.14 (s, 1H, H-6), 7.67-7.70 9 m, 4H-Ar-H), 7.41-7.50 (m, 6H-Ar-H), 6.28 (dd, J=5.6 Hz, and 2.4 Hz, 1H, H-1'), 4.68 (d, J=8.8 Hz, $OCH_2N$), 4.61 (d, J=8.8 Hz, 1H, $OCH_2N$), 4.38-4.39 (1H, H-3'), 4.08-4.09H (m, 1H, H-4'), 4.00-4.04 (m, 1H, H-5'), 3.79-3.82 (m, 1H, H-5'), 2.57-2.62 (m, 1H, H-2') 2.13-2.20 9 m, 1H, H-5') 1.10, (s, 9H, $CH_3x3$); Mass calc for $C_{31}H_{33}F_3N_{66}Si$, 670, Found (M+H) 671.

Synthesis of 5'-O-tert-butyldiphenylsilyl-3'-O-azidomethyl-5-[3-amino-prop-1ynyl]-2'deoxyuridine (25). A solution of 24 (0.25 g) in methanolic ammonia (7N, 50 mL) was heated in a sealed tube for 3 h at 55° C. Reaction was cooled to room temp and concentrated to afford a white foam (0.21 g, 98%). 1H-NMR (CDCl$_3$) δ 8.13 (s, H-6), 7.67-7.69 (m, 4H, Ar-H), 7.42-7.62 (m, 6H, Ar-H), 6.28-6.35 (m, 1H-H-1'), 4.59-4.69 (m, 2 h, $OCH_2$—N), 4.38 9 m, 1 h, H3'), 4.15-4.17 (m, 1H, H-4'), 3.99-4.01 (m, 1H, H-5'), 3.78-3.81 (m, 1H, 5-H), 3.40 9 s, $CH_2N$), 2.54-2.64 (m, 1H, H-2'), 2.11-2.18 (m, 1H, H-2'), 1.10 (s, 9H, $C(CH_3)_3$), Mass calcd for $C_{29}H_{34}N_6O_5Si$, 574.2, Found (M+H), 575.

2-(Pyridin-2y1-disulfanyl)-ethanol (26). 2-Mercaptoethanol (3.9 g, 49.9 mmol) was added to a solution of 2-2'-dipyridyl-disulphide B (10 g, 45.4 mmol) in pyridine/Methanol (3:200 mL) and mixture was stirred overnight. The mixture was evaporated to dryness and the residue was purified by flash chromatography on silica gel. The desired product was eluted with 30-50% ethyl acetate in Hexanes as colorless oil (4.5 g, 53%). 1H-NMR (CDCl$_3$) δ 8.51 (d, J=4.0 Hz, 1H, Ar-H), 7.57-7.62 (m, 1H-Ar-H), 7.40-7.62 (m, 1H, Ar-H), 7.15-7.28 (m, 1H, Ar-H), 5.84 (br s, 1 h, OH), 3.81 (t, J=5.2 Hz, 2H, $OCH_2$), 2.96 (t, J=5.2 Hz, $SCH_2$), Mass calcd for $C_7H_9NOS_2$ 187, Found (M+H), 188.

2-(N-tert-butoxyamido-ethyl) 2-yl-disulfanyl)ethanol (27). To a solution of 26 (0.9 g, 4.8 mmol) in methanol/pyridine (40/1 mL) was added BOC-cysteamine (2.1 g, 11.8 mmol) and the mixture was stirred overnight. The reaction was concentrated and the residue was purified by flash chromatography on silica gel. The desired product was obtained with 40-60% ethanol in hexanes gradient as colorless oil (1.04 g, 86%). 1H-NMR (CDCl3) δ 4.89 (br s, 1H, OH), 3.88-3.91 (t, J=5.6 Hz, 2H, $OCH_2$), 3.46-3.48 (m, 2H, $NCH_2$), 2.88-2.91 (t, J=6.0 $H_z$, 2H, $SCH_2$), 2.80-2.2.83 (t, J=6.8 Hz, 2H, $SCH_2$), 1.45 (s, 9H, $C(CH_3)_3$). Mass calcd for $C_9H_{19}NO_3S_2$, 253.0, Found (M+Na) 276.

2-(N-tert-butoxyamido-ethyl) 2-yl-disulfanyl)ethyl-4-nitrophenyl carbonate (28). To a cooled (4° C.) of 27 (0.80 g, 3.16 mmol) in anhydrous acetonitrile, triethyl amine (540 uL, 3.82 mol) and a solution of 4-nitrophenylcarbonate (0.75 g, 3.72 mmol) in acetonitrile was added slowly during 10 minute under nitrogen. Reaction was stirred further overnight at room temperature. After removing the volatiles, the crude residue was purified by flash chromatography on silica gel. The desired product was eluted as white crystalline solid (1.05 g, 75%). 1H-NMR (CDCl$_3$) δ 8.30 (d, J=9.2 Hz, 2H, Ar-H), 7.41 (d, J=9.2 Hz, 2H, Ar-H), 4.55-4.58 (t, J=6.8 Hz, 2H, $OCH_2$), 3.48-3.49 (m, 2H, ($NCH_2$), 3.02-3.06 (t, J=6.8 Hz, 2H, $SCH_2$), 2.84-2.87 (t, J=6.0 Hz, 2H, $SCH_2$), 1.46 s, 9H, $C(CH_3)_3$), Mass calcd for $C_{16}H_{22}N_2O_7S_2$(M+Na) 441, Found, 441.

Synthesis of 5'-O-tert-butyldiphenylsilyl-3'-O-azidomethyl-5-[3 (2-(N-tert-butoxyamido-ethyl)-2-yl-disulfanyp-ethyloxy-caroxyamido)-prop-1-ynyl]-2'deoxyuridine (29). To a solution of 25 (0.35 g, 0.61 mmol) in $NaHCO_3/Na_2CO_3$ buffer (pH 9.2, 2.0 mL), a solution of 28 (0.34 g, 0.77 mmol) in acetonitrile (5 mL) was added and the reaction was stirred overnight. Reaction was diluted with ethyl acetate, and washed with brine. Organic layer was separated, dried over anhyd. $MgSO_4$ and concentrated. The residue was purified by flash chromatography on silica gel. The desired product was eluted with EA in Hexanes (50 to 75% gradient) as white solid (0.36 g, 71%). 1H-NMR (CDCl$_3$) δ 8.03 (s, 1H, H-6), 7.67-7.70 (m, 4H, Ar-H), 7.42-7.51 (m, Ar-H-6H), 6.25-6.29 (t, J=6.0 Hz, 1H, H-1'), 4.66-4.69 (d, J=9.2 Hz, 1H, $NCH_2$), 59-4.61 (d, J=9.2 Hz, 1H, $NCH_2$), 4.36-4.38 (m, 1H, H-3'), 4.29-4.32 (t, J=6.0 Hz 1H, $OCH_2$), 4.37-4.0 (m, 3H, $NCH_2$ and H-5'), 3.79-3.82 (m, 1H, H-5'), 3.45-3.37 (m, 2H, $NCH_2$), 2.87-2.91 (t, J=6.0 HZ, 2H, $SCH_2$), 2.79-2.82 (t, J=6.4 Hz, 2H, $SCH_2$), 2.54-2.59 (m, 1H, H-2'), 2.11-2.18 (m, 1H, H-2'), 1.46 (s, 9H, $O(CH_3)_3$), 1.01 (s, 9H, $C(CH_3)_3$); Mass calcd for C23H36N7O18P3S2 (M+Na), 876, found 876.

Synthesis of 3'-O-azidomethyl-5'-hydoxy-5-[3(2-(N-tert-butoxyamido-ethyl)-2-yl-disulfanyl)ethyloxy-caroxyamido)-prop-1-ynyl]-2'deoxyuridine (30). To a solution of 29 (0.30 g, 0.35 mmol) in anhyd. THF (10 mL) was added a solution of triethylamine trihydrofluoride 90.29 g, 0.29 mmol) and mixture was heated for 3 h at 55° C. The volatiles were removed and oily residue was purified by flash chromatography on silica gel. The desired product was eluted with 0-55% methanol in ethyl acetate as white solid (0.22 g, 76%). 1H-NMR (CDCl$_3$) δ 8.22 (s, 1H, H-6), 6.21-6.24 (t, J=6.4 Hz, 1H, H-1'), 5.50 (br s, 1H, OH), 4.76-4.78 (d, J=8.8 Hz, 1H, $N_3CH_2$), 4.69-4.71 (d, J=9.6 Hz, 1H, $N_3CH_2$), 4.49-4.51 (m, 1H, H-3'), 4.34-4.36, m (1H, 2H, $OCH_2$), 4.17-4.19 (m, 3H, $NCH_2$ and H-4'), 4.01-4.01 (d, J=11.2 Hz, 1H, $NCH_2$), 3.87-3.89 (d, J=10.0 Hz, 1H, $NCH_2$), 3.45-3.47 (m, 2H, H-5'), 3.09-3.10 (m, 2H, SCH2), 2.81-2.83 (m, 2H, SCH2), 2.50-2.52 (m, 1H, H-2'), 2.31-2.34 (m, 1H, H-2'), 1.47 (s, 9H, $O(CH_3)_3$), Mass calcd for $C_{23}H_{33}N_7O_9S_2$(M+Na) 638, found 638.

Synthesis of 3'-O-azidomethyl-5-[3(2-(N-tert-butoxyamido-ethyl)-2-yl-disulfanyl)ethyloxy-carboxyamido)-prop-1-ynyl]-2'deoxy-uridine-triphosphate (31). To a solution of 30 in anhyd. THF and anhyd. pyridine (5 mL each), a solution of 2-chloro-$H-1,3,2-benzodioxaphosphorin-4-one (0.0.090 g, 0.45 mmol) dissolved in 1 mL THF) was added under nitrogen and stirred for 1.5 h (TLC didn't show any starting material). Tributylamine (0.35 g, 1.95 mmol) and tributyl-ammonium pyrophosphate (0.05 mmol solution in DMF, 1.3 mL, 0.65 mmol) were added subsequently and stirred further for 3 h. tert-butylhydrogenperoxide solution (5.5 m solution in decane, 350 ul, 1.92 mmol) was added to reaction and stirred further for 1 h. The reaction was then quenched with water and left overnight. The LCMS of the crude reaction showed 27% of the desired product. It was purified by ion exchange HPLC using Dionex DNA Pac column (9×250 mm) and 50 mM TRIS as buffer A and 50 mM tris and 800 mM ammonium chloride as buffer B with a gradient of 0-40% B in 30 min. Mass calcd for $C_{23}H_{36}N_7O_{18}P_3S_2$ 855.08, Found LCMS 855.1.

Synthesis of 3'-O-azidomethyl-5-[3-(2-aminoethyl)-2-yl-disulfanyl)-ethyloxy-carboxyamido)-prop-1-ynyl]-2'deoxy-uridine-triphosphate (32). Aqueous trifluroacetic acid solution (58 uL in 52 uL water) was added to a solution of 31 (7.56 uMols) and stirred for 4 h. The desired product was isolated by reverse phase HPLC using Hamilton PRP-column (21.2×250 mm) and 50 mm triethylammonium bicarbonate as buffer A and Acetontrile as buffer B using a gradient of 0-40% B in 30 minutes. Mass calcd for $C_{18}H_{28}N_7O_{16}P_3S_2$, 755.02, Found LCMS 754.9.

Synthesis of Fluorescein Labeled Terminator (33). To a solution of 32 (3.16 uM) in sodium carbonate/sodium bicarbonate buffer (pH 9.2, 600 uL), a solution of 5-carboxyfluorescein succinimidyl ester (15 mg, 31.6 uM) in DMSO (50 uL) was added. The reaction was stirred overnight. The crude product was purified by reverse phase HPLC using 50 mM triethyl ammonium bicarbonate as buffer A and acetonitrile as buffer B using a gradient of 0-40% B in 30 min. the reddish powder was characterized by LCMS, calc mass $C_{39}H_{38}N_7O_{22}P_3S_2$, 1113.07, found LCMS 1112.9.

Example 2

Synthesis of 3'-O-azidomethyl-5-(Alexa530-dithiolinker-carbamate)-dUTP (34)

Figure 7:
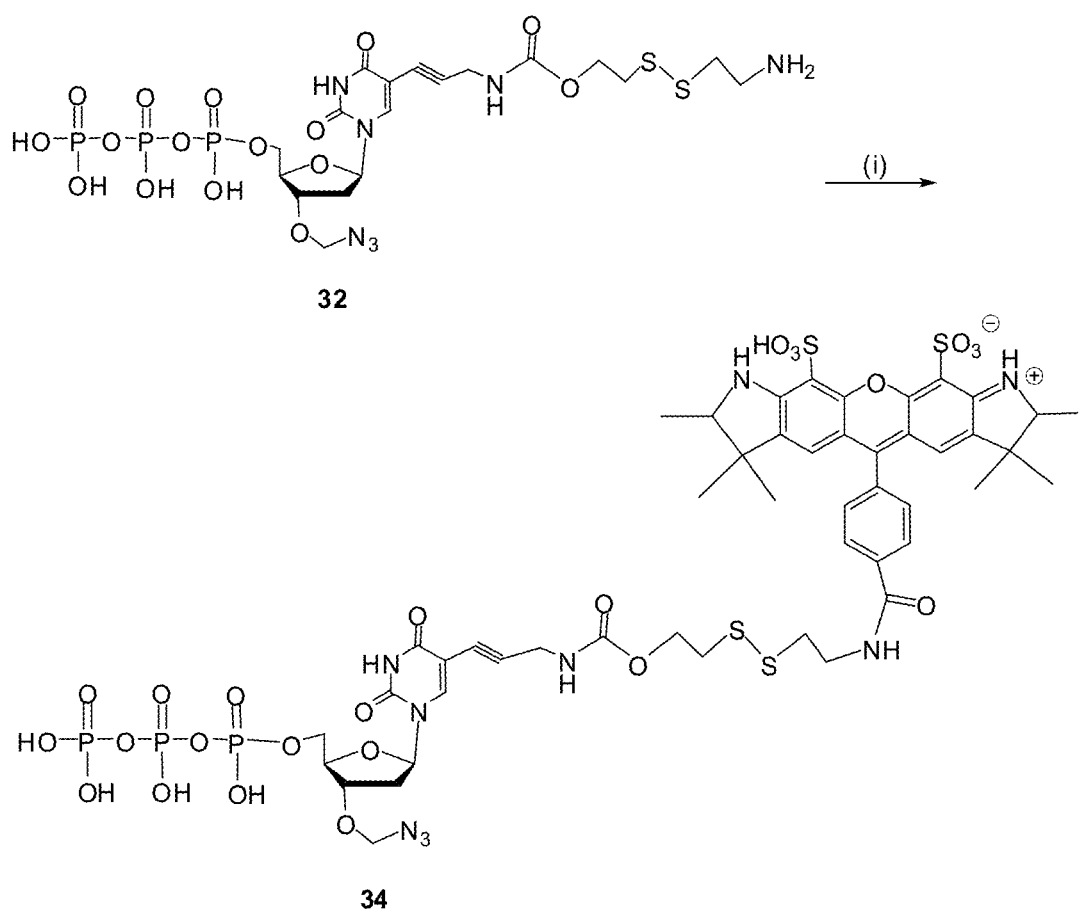
FIG. 7 illustrates the synthetic route for the preparation of a reversible terminator with Alexa-530 as its fluorophore, according to the present disclosure.

The title compound was prepared according the methods shown in FIG. 7. Specifically, reagents and conditions used in FIG. 7 are: (i) Alexa Fluor® 530 NHS ester (dihydrogen 5-(4-{[(2,5-dioxo-1-pyrrolidinyl)oxy]carbonyl}phenyl)-2,3,3,7,7,8-hexamethyl-2,3,7,8-tetrahydro-1H-pyrrolo[3',2':6,7]chromeno[3,2-f]indole-10,12-disulfonate), borate buffer (pH 9.0).

Synthesis of Alexa-530 labeled terminator (34). To a solution of 32 (1.18 uM) in borate buffer (pH 9.0, 200 uL) was added Alexa Fluor• 530 NHS ester (dihydrogen 5-(4-{[(2,5-dioxo-1-pyrrolidinyl)oxylcarbonyl}phenyl)-2,3,3,7,7,8-hexamethyl-2,3,7,8-tetrahydro-1H-pyrrolo[3',2':6,7]chromeno[3,2-f]indole-10,12-disulfonate) (2.2 mg, 3.0 uMol) and stirred overnight. The crude product was purified from reverse phase HPLC using 50 mM triethyl ammonium bicarbonate as buffer A and acetonitrile as buffer B using a gradient of 0-40% B in 30 min. the reddish powder was characterized by LCMS, calc mass $C_{48}H_{56}N_9O_{24}P_3S_4$, 1163.15, found LCMS 1162.9.

Example 3

Synthesis of 3'-O-azidomethyl-5-(Alexa647-dithiolinker-carbamate)-deoxycytidinetriphosphate (45)

Figure 8:
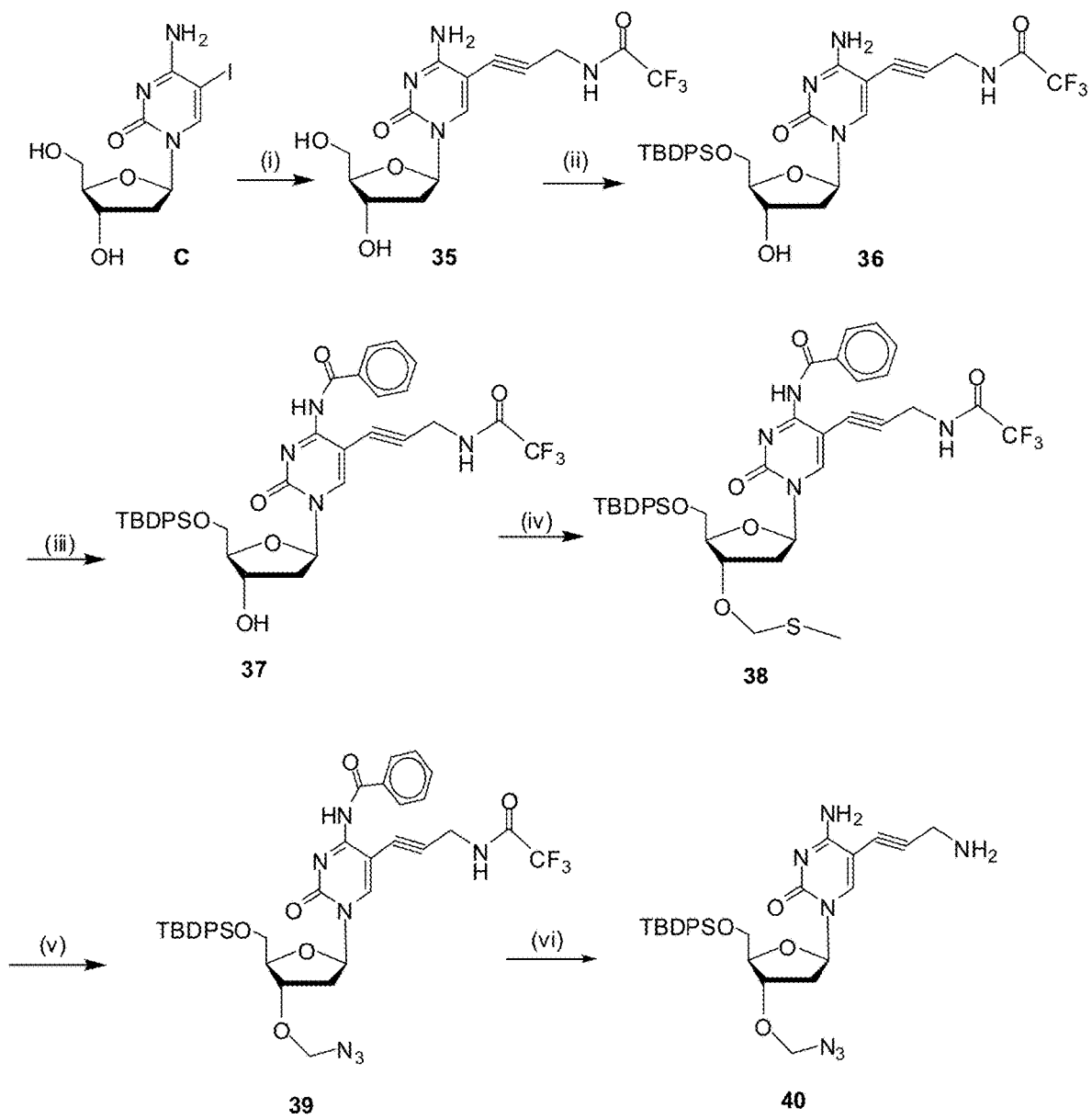
FIGS. 8 and 9 depict the synthetic route for the preparation of a reversible terminator with Alexa-647 as its fluorophore, according to the present disclosure.
Figure 9:
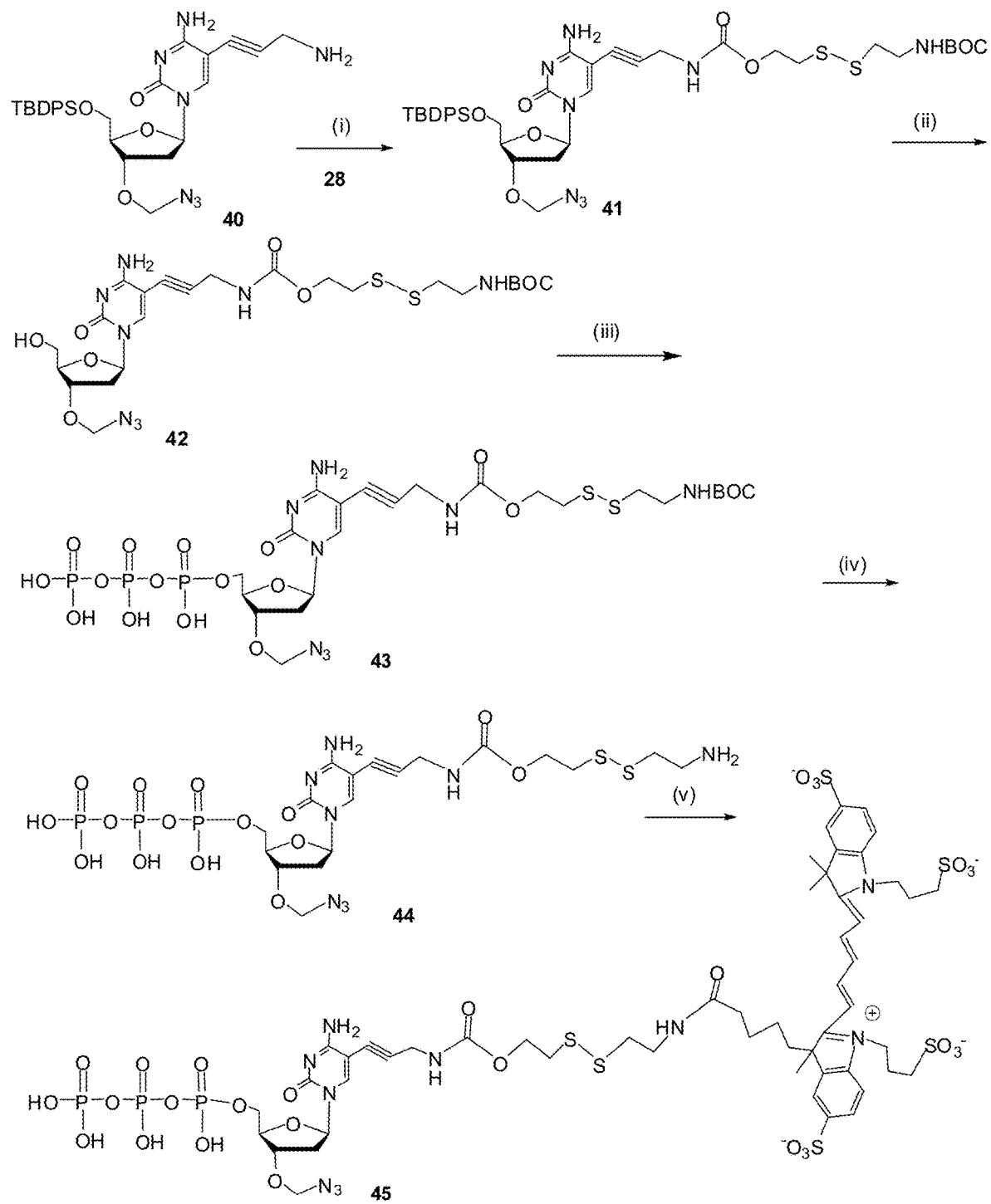

The title compound was prepared according the methods shown in FIGS. 8-9. Specifically, reagents and conditions used in FIG. 8 are: Reagents and conditions: (i) N-trifluoroacetylpropargylamine, Pd(PPh$_3$)$_4$, CuI, triethylamine, DMF, RT, 12 h, (ii) tertbutyl-diphenylsilylchloride, pyridine, RT, 12 h, (v) a) $SO_2Cl_2$, 0° C., pyridine, (b) benzoyl chloride; (iv) DMSO, AcOH, Ac$_2$O, RT, 12 h, (v) a) SOC C, 0° C., h; b) NaN$_3$, DMF, 4 h, (vi) methanolic ammonia, 55° C., 3 h; and reagents and conditions used in FIG. 9 are: 28, NaHCO$_3$/Na$_2$CO$_3$ buffer (pH 9.2), acetonitrile, (ii) Et$_3$N.3HF, THF, 55 C, 4 h, (iii) (a) 2-chloro-1H-1,3,2-benzodioxaphosphorin-4-one, pyridine, THF, 1.5 h, (b). tributylamine, tributylammonium pyrophosphate, 4 h; (c) tert-butyl hydrogen peroxide 1 h, (iv) Aq TFA, (v). Alexa Fluor® 647 NHS ester (3-(2-((1E,3E)-5-((E)-3,3-dimethyl-5-sulfo-1-(3-sulfopropyl)indolin-2-ylidene)penta-1,3-dien-1-yl)-3-(5-(2,5-dioxopyrrolidin-1-yl)-5-oxopenty)-3-methyl-5-sulfo-3H-indol-1-ium-1-yl)propane-1-sulfonate), borate buffer.

Synthesis of N-(3-(4-amino-1-((2R,4S,5R)-4-hydroxy-5-(hydroxymethyl)tetrahydrofuran-2-yl)-2-oxo-1,2-dihydropyrimidin-5-yl)prop-2-yn-1-yl)-2,2,2-trifluoroacetamide (35). To a solution of 5-iodocytidine C (7.5 g, 21.2 mmol) in anhyd DMF (75 mL) CuI (0.30 g, 1.57 mmol) and Pd(PPh$_3$)$_4$ (0.62 g, 0.053 mmol) were added. After stirring for 10 min. triethylamine (6.0 mL, 42.9 mmol) and N-trifluoroacetylpropargylamine (9.6 g, 63.5 mmol) were added. The reaction mixture was stirred overnight at room temperature. All the volatiles were removed under vacuum and the residue was purified by flash chromatography on silica gel (EtOAc/MeOH (0-15%)] to afford the desired product 35 as yellow solid 7.8 g (79%). 1H-NMR (DMSo-d6) δ 9.97 (brs, 1H, NH), 8.15 (s, 1H, H-6), 6.08-6.12 (t, J=6.4 Hz, 1H, H-1'), 5.20-5.21 (d, J=4 Hz, 1H, OHO, 5.05-5.07 (t, J=4.8 Hz, 1H, OH), 4.28-4.29 (d, J=5.2 Hz, 2H, $NCH_2$), 4.15-4.19 (m, 1H, H-3'), 3.77-3.79 (m, 1H, H-4'), 2.11-2.16 (m, 1H, (H-2'), 1.92-1.96 (m, 1H, H-2').

Synthesis of N-(3-(4-amino-1-((2R,4S,5R)-5-(((tert-butyldiphenylsilyl)oxy)methyl)-4-hydroxytetrahydrofuran-2-yl)-2-oxo-1,2-dihydropyrimidin-5-yl)prop-2-yn-1-yl)-2,2,2-trifluoroacetamide (36). Tert-butyldiphenylsilyl chloride (6.97 mL, 26.65 mmol) was added dropwise to a stirred solution of compound 35 (9.11 g, 24.23 mmol) in dry pyridine (100 mL) at 0° C. under N$_2$. After 10 minutes, the solution was allowed to rise to room temperature and stirred overnight. The volatiles were removed under vacuum and the residue was purified by flash chromatography on silica using ethyl acetate in hexanes from 75-100% to afford the desired product 36 (8.42 g, 57%). 1H-NMR (DMSO-d6) δ 7.95 (s, 1H, H-6), 7.61-7.65 (m, °° 4H, Ar-H), 7.43-7.47 (m, 6H, Ar-H), 6.11-6.15 (t, J=6.8 Hz, H-1'), 5.26-5.28 (m, 1H, OH), 4.20-4.27 (m, 1H, H-3'), 4.13-4.15 (d, J=4.8 Hz, $NCH_2$), 3.84-3.90 (m, 3H, H-4 and $CH_2$-5'), 3.70-3.74 (m, 1H, $CH_2$-5'), 1.00 (s, (H, $C(CH_3)_3$)

Synthesis of N-(1-((2R,4S,5R)-5-(((tert-butyldiphenylsilyl)oxy)methyl)-4-hydroxytetrahydrofuran-2-yl)-2-oxo-5-(3-(2,2,2-trifluoroacetamido)prop-1-ynyl)-1,2-dihydropyrimidin-4-yl)benzamide (37). The compound 36 (4.06 g, 6.6 mmol) was azeotroped in dry pyridine, then dissolved in dry pyridine (40 mL) under $N_2$ atmosphere. Chlorotrimethylsilane (2.3 mL, 26.4 mmol) was added drop wise to the solution and stirred for 2 hours at room temperature. The reaction mixture was cooled down to 0 C and benzoyl chloride (0.81 mL, 6.94 mmol) was added drop wise to the reaction mixture. The reaction mixture was kept at 0 C for 1 hour. Then water (20 mL) was added slowly to the reaction mixture and kept stirring at room temperature overnight. All the volatiles were removed on vacuum and the residue was portioned between sat. aq. $NaHCO_3$ solution and EtOAc. The organic phase was separated and the aqueous phase extracted with a further of EtOAc. The organic layers were combined, dried ($MgSO_4$), filtered and concentrated on vacuum. The residue was purified by flash chromatography on silica using 20-60% EA in hexanes to give desired product 37 (2.74 g, 58%). 1H-NMR ($CDCl_3$) δ 8.34 (s, 1H, H-6), 8.22-8.25 (m, 2H, Ar-H), 7.80-7.7.83 (m, 4H, Ar-H), 7.43-7.50 (9H, Ar-H), 6.33-6.36 (t, J=6.0 Hz, 1H, H-1'), 4.52-4.54 (m, 1H, H-3'), 4.03-4.17 (m, 4H, $NCH_2$, H-4', H-5'), 3.77-3.83 (m, 1H, H-5'), 2.56-2.60 (m, 1H, H-2'), 2.25-2.30 (m, 1H, H-2'), 1.10 (s, 9H, $C(CH_3)_3$).

Synthesis of N-(1-((2R,4S,5R)-5-(((tert-butyldiphenylsilyl)oxy)methyl)-4-((methylthio)methoxy)tetrahydrofuran-2-yl)-2-oxo-5-(3-(2,2,2-trifluoroacetamido)prop-1-yn-1-yl)-1,2-dihydropyrimidin-4-yl)benzamide (38). The compound 37 (5.25 g, 7.31 mmol) was dissolved in dry DMSO (28 mL) under $N_2$ atmosphere. Acetic acid (5.7 mL, 0.10 mol) and acetic anhydride (18.0 mL, 0.19 mol) were added sequentially and slowly to the solution. The reaction mixture was stirred at room temperature overnight. The volatiles were removed under vacuum and the residue was dissolved in EtOAc (200 mL) and then poured into Saturated $NaHCO_3$ solution (250 mL) and stirred for one hour. The aqueous layer was extracted with EtOAc (100 mL). The organic layers were combined, dried ($MgSO_4$), filtered and concentrated. The crude product was purified by flash chromatography (EtOAc:Hexane, 0 to 30%) to yield the titled compound 38 (2.55 g, 45%), 1H-NMR ($CDCl_3$) δ 8.30 (s, 1H, H-6), 8.22-8.25 (m, 2H, Ar-H), 7.64-7.73 (m, 4H, Ar-H), 7.39-7.50 (m, 9H, Ar-H), 4.51-4.65 (m, 3H, $SCH_2$ and H-3'), 4.16-4.18 (m, 1H, H-3'), 4.02-4.09 (m, 2H, $NCH_2$), 4.02-4.05 (m, 1H, H-5'), 3.80-3.83 (m, 1H, H-5'), 2.64-2.67 (m, 1H, H-2'), 2.06-2.20 (m, 4H, $SCH_3$ and H-2'), 1.10 (s, 9H, $C(CH_3)_3$).

Synthesis of N-(1-((2R,4S,5R)-4-(azidomethoxy)-5-(((tert-butyldiphenylsilyl)oxy)methyl)tetrahydrofuran-2-1)-2-oxo-5-(3-(2,2,2-trifluoroacetamido)prop-1-yn-1-yl)-1,2-dihydropyrimidin-4-yl)benzamide (39). Synthesis of The starting material 38 (2.55 g, 3.28 mmol) was dissolved in dry DCM (20 mL) and cooled to −78° C. Cyclohexene (1.66 mL, 16.39 mmol) and $SO_2Cl_2$ (9.8 mL, 9.83 mmol) were added. The reaction mixture was stirred for one hour. Volatiles were removed under vacuum. To the residue was added $NaN_3$ (1.06 g, 16.39 mmol) and dry DMF (20 mL) and then stirred for 2 hours at room temperature. TLC indicated that the reaction was complete. The reaction was passed through a pad of silica gel and washed with EtOAc. Removed the solvent under vacuum. The residue was purified by flash chromatography (EtOAc:Hexane, 0 to 30%) to yield the titled compound 39 (1.37 g, 54%). 1H-NMR ($CDCl_3$) δ 8.26 9 s, H-6'), 8.21-8.23 9 m, 2 h, Ar-H), 7.45-7.70 (m, 4H, Ar-H), 7.40-7.48 (m, 9H, Ar-H), 6.25-6.28 (q, J=5.6, 2.4 Hz, 1H, H-1'), 4.66-4.69 (d, J=9.2 Hz, 1H, $NCH_2$), 4.55-4.58 (d, J=9.2 Hz, 1H, $NCH_2$), 4.35-4.37 (m, 1H, H3'), 4.16-4.18 (m, H-4'), 4.10-4.13 (t, J=4.0 Hz, 2H, $NCH_2$), 4.00-4.04 (m, 1H, H-5'), 3.80-3.84 (m, 1H, H-5'), 2.62-2.67 (m, 1H, H-2') 2.03-2.18 (m, 1H, H-2'), 1.10 (s, 9H, $C(CH_3)_3$).

Synthesis of N-(5-(3-aminoprop-1-yn-1-yl)-1-((2R,4S,5R)-4-(azidomethoxy)-5-(((tert-butyldiphenylsilyl)oxy)methyl)tetrahydrofuran-2-yl)-2-oxo-1,2-dihydropyrimidin-4-yl)benzamide (40). A solution of 39 (0.60 g, 0.77 mmol) in methanolic ammonia (40 mL) was heated in a sealed tube at 55° C. for 1 h (TLC showed no starting material). The solution was cooled to room temperature and concentrated. The residue was purified by flash chromatography and the desired product was eluted with Methanol in ethyl acetate (0-15%) to yield the desired product 20 (0.28 g, 54%). 1H-NMR ($CDCl_3$) δ 8.12 (s, 1H, H-6), 7.66-7.77 (m, 4H, Ar-H), 4.40-4.49 (m, 6H, Ar-H), 4.69-4.71 (d, J=8.8 Hz, 1H, $CH_2N_3$), 4.54-4.56 (d, J=8.8 Hz, 1H, $CH_2N_3$), 4.36-4.39 (m, 1H, H-3'), 4.13-4.16, m, 1H, H-4'), 3.96-4.00 (m, 1H, H-5'), 3.77-3.80 (m, 1H, H-5'), 3.45-3.50 (m, 2H, $NCH_2$), 4.67-4.72 (m, 1H, H-2'), 2.06-2.19 (m, 1H, H-2'), 1.10 (s, 9H, $C(CH_3)_3$).

Synthesis of 2-((2-((tert-butoxycarbonyl)amino)ethyl)disulfaneyl)ethyl (3-(1-((2R,4S,5R)-4-(azidomethoxy)-5-(((tert-butyldiphenylsilyl)oxy)methyl)tetrahydrofuran-2-yl)-4-benzamido-2-oxo-1,2-dihydropyrimidin-5-yl)prop-2-ynyl)carbamate (41). To a solution of 40 (0.31 g, 0.54 mmol) in $NaHCO_3/Na_2CO_3$ buffer (pH 9.2, 5.0 mL), a solution of 28 (0.30 g, 0.68 mmol) in acetonitrile (5 mL) was added and the reaction was stirred overnight. Reaction was diluted with ethylacetate, washed with brine. Organic layer was separated, dried over anhyd. $MgSO_4$ and concentrated. The residue was purified by flash chromatography on silica gel. The desired product was eluted with EA in MeOH (0-10%) as white solid (0.30 g, 65%). 1H-NMR ($CDCl_3$) δ 8.13 (s, 1H, H-6), 7.66-7.71 (m, 4H, Ar-H), 7.41-7.52 (m, 6H, Ar-H), 6.25-6.28 (t, J=7.2 Hz, 1H, H-1'), 4.68-4.71 (d, J=8.8 Hz, 1H, $N_3CH_2$), 4.57-4.55 (d, J=8.8 Hz, 1H, $N_3CH_2$), 4.32-4.37 (m, 3H, $NCH_2$ and H-3'), 4.15-4.17 (m, 1H, H-4'), 3.97-4.01 (m, 2H, $NCH_2$), 3.79-3.83 (m, 1H, H-5'), 3.44-3.49 (m, 1H, H-5'), 3.44-3.49 (m, 2H, $NCH_2$), 2.92-2.95 (t, J=6.4 Hz, 2H, $SCH_2$), 2.79-2.83 (t, J=6.4 Hz, 2H, $SCH_2$), 2.68-2.72 (m, 1H, H-2'), 2.06-2.12 (m, 1H, H-2'), 1.10 (s, 9H, $C(CH_3)_3$).

The compound 45 is synthesized according to steps described in FIG. 9 from compound 41, similar to those steps used when preparing compound 33.

Example 4

Synthesis of 3'O-azidomethyl-7-deaza-5-(alexa568-dithiolinker-carbamate)-7-deaza-2' deoxyadenosinetriphosphate terminator (59)

Figure 10:
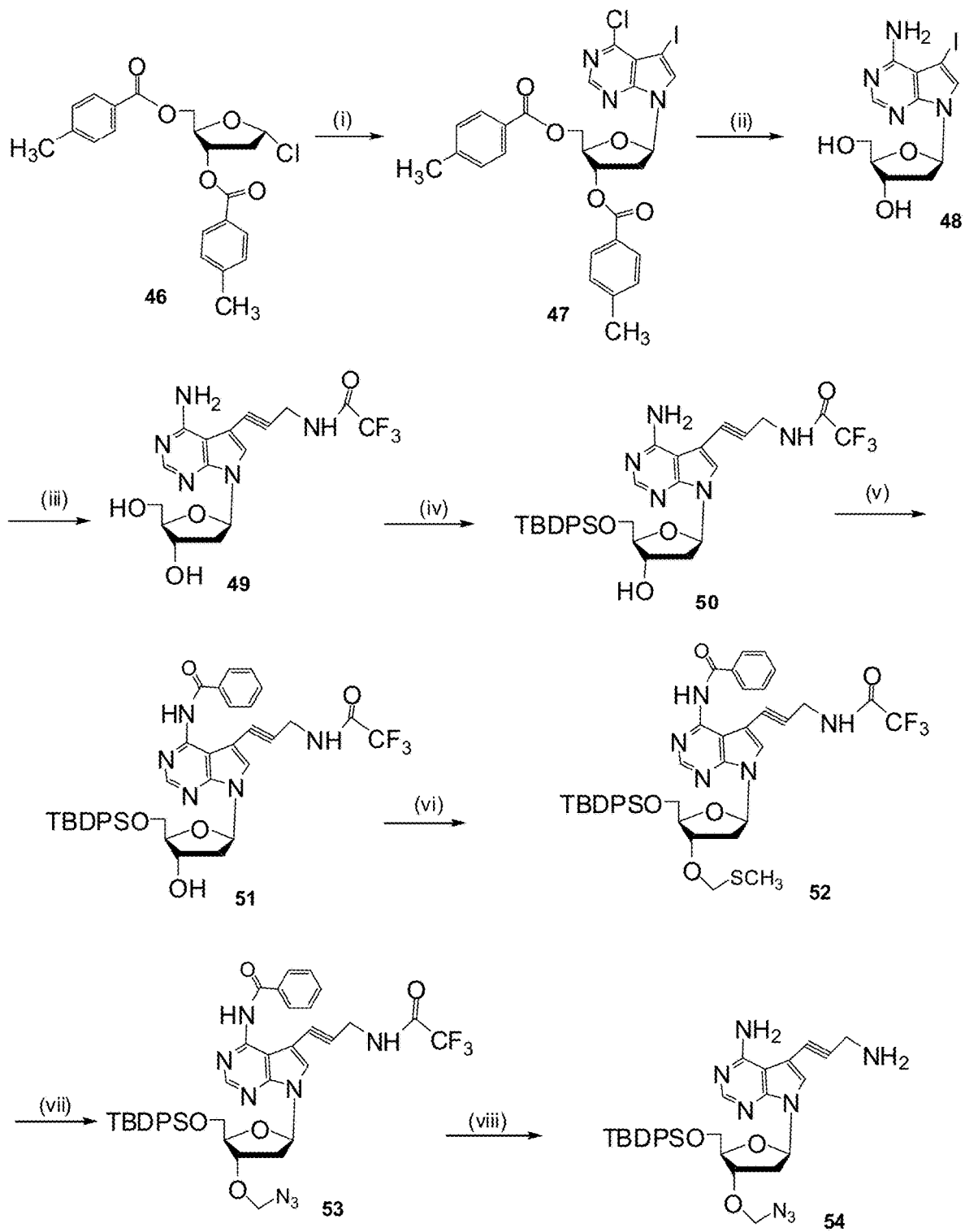
FIGS. 10 and 11 portrait the synthetic route for the preparation of a reversible terminator with Alexa-647 as its fluorophore, according to the present disclosure.
Figure 11:
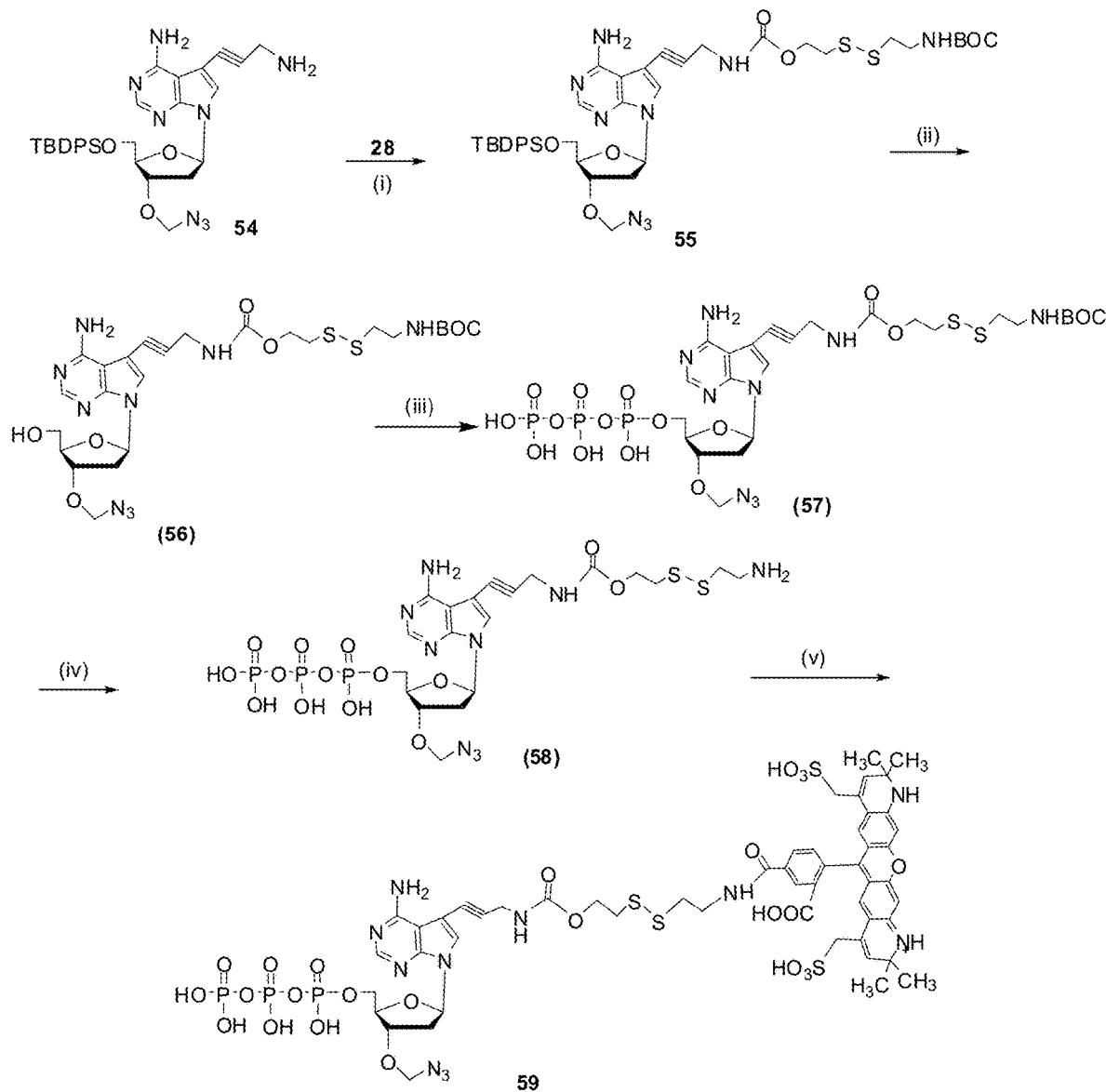

The title compound was prepared according the methods shown in FIGS. 10-11. Specifically, reagents and conditions used in FIG. 10 are: Reagents and conditions: (i) 4-chloro-5-iodo-7H-pyrrolo[2,3-d]pyrimidine, NaH, ACN; (ii) NH$_4$OH, MeOH, (iii). N-trifluoroacetylpropargylamine, Pd (PPh$_3$)$_4$, CuI, triethylamine, DMF, RT; (iv). tert-butyl-diphenylsilylchloride, pyridine; (v). (a) chlorotrimethylsilane, pyridine, (b) benzoyl chloride (vi) DMSO, AcOH, Ac$_2$O; (vii). a) SO$_2$C$_2$, 0° C., b) NaN$_3$, DMF (viii) MeOH, ammonia; and reagents and conditions used in FIG. 11 are: 28, NaHCO$_3$/Na$_2$CO$_3$ buffer (pH 9.2), acetonitrile, (ii) Et$_3$N.3HF, THF, 55 C, 4 h, (iii) (a) 2-chloro-1H-1,3,2-benzodioxaphosphorin-4-one, pyridine, THF, 1.5 h, (b). tributylamine, tributylammonium pyrophosphate, 4 h; (c) tert-butyl hydrogen peroxide, 1 h, (iv) Aq TFA, (v). Alexa Fluor® 568 NHS ester ([6-(2-Carboxy-5-{[(2,5-dioxo-1-pyrrolidinyl)oxy]carbonyl}phenyl)-2,2,10,10-tetramethyl-8-(sulfomethyl)-10,11-dihydro-2H-pyrido[3',2':6,7]chromeno[3,2-g]quinolin-1-ium-4-yl]methanesulfonate), NaHCO$_3$/Na$_2$CO$_3$ buffer (pH 9.2).

The compound 59 is synthesized according to the above steps, similar to steps used when preparing compound 33.

Procedure for Primer Extension Assays

Oligo Preparation: Oligos were purchased from IDT and stored at 500 uM in nuclease-free water: A biotinylated target sequence (Biot_Primer1_Capt, 5'-/5Biosg/CTGAAC-GGTAGCATCTTGACGAGATCGGAAGAGCGTCGTGT-AGGGAAAGAGTG TTTCAG-3' (SEQ ID NO: 1)) and a sequencing primer (SP_T, 5'-ACTCTTTCCCTACA-CGACGCTCTTCCGATCTCG-3' (SEQ ID NO: 2)). 8 nmol of the biotinylated template sequence was conjugated to streptavidin-coated magnetic beads (T1 Dynabeads, Invitrogen) for one hour at room temperature in a solution containing 1M NaCl, 10 mM Tris-HCl pH7.5, 1 mM EDTA. Beads were washed three times with wash buffer at 60° C. (0.64×SSC, 0.016% SDS) to remove unbound primer and stored in 800 µL reaction binding buffer, RB, (1M NaCl, 25 mM Tris-HCl pH7.5, 0.01% TWEEN20) at 4° C. To hybridize the sequencing primer to the template, 100 uL of conjugated beads were incubated with a saturating amount of SP_T (2.5 nmol) in 200 µL RB at 70° C. for five minutes, 55° C. for 15 minutes, then 25° C. for 5 minutes. Hybridized beads were stored in 360 uL RB at room temperature.

Primer extension: For reactions with CENT1 enzyme, the enzyme was boiled for 5 minutes at 95° C. before use. 40 uL of hybridized beads were resuspended in 22.5 uL of reaction mixture (40 mM Tris-HCl pH8.8, 20 mM ammonium sulfate, 20 mM KCl, 0.2% Triton X-100, 2 mM MgSO$_4$, 1.5 ug CENT1). Reactions were pre-warmed to 45° C. for one minute before adding 2.5 uL of 20 uM nucleotide (for a final concentration of 2 uM). After one minute of incorporation, reactions were quenched with 40 µL RB. Beads were washed with 40 µL RB and either resuspended in a new reaction mixture for further incorporation events or SP_T was eluted with 0.1 N NaOH for 10 minutes at room temperature then neutralized with 1.5 uL Tris-HCl pH8.0. For reactions with Bst large fragment (NEB), 40 uL of hybridized beads were resuspended in 22.5 uL of reaction mixture (40 mM Tris-HCl pH8.8, 20 mM ammonium sulfate, 20 mM KCl, 0.2% Triton X-100, 2 mM MgSO$_4$, 40 U Bst). Reactions were pre-warmed to 37° C. for one minute before adding 2.5 uL of 1 mM dNTPs (NEB) (for a final concentration of 100 uM). After five minutes at 37° C., reactions were quenched with 40 µL RB. Beads were washed with 40 µL RB and SP_T was eluted with 0.1N NaOH for 10 minutes at room temperature then neutralized with 1.5 uL Tris-HCl pH8.0.

Cleavage of Reversible Terminators: After incorporation of reversible terminators, beads were resuspended in 100 mM TCEP pH9.0 (Gold Bio) and incubated at 65° C. for 30 minutes before quenching with 100 µL RB. Beads were washed with 40 µL RB and either resuspended in a new reaction mixture for further incorporation events or SP_T was eluted with 0.1N NaOH for 10 minutes at room temperature then neutralized with 1.5 uL Tris-HCl pH8.0.

Denaturing PAGE: An equal volume of 2×TBE-Urea Sample Buffer (Novex, Thermo Fisher) was added to samples before heat-denaturation for five minutes at 85° C. 10 µL sample and a 10 bp ladder (TrackIt, Invitrogen) on a 15% TBE-Urea PAGE gel (Novex, Thermo Fisher) in 1×TBE for two hours at 160V. Gels were imaged for fluorescence before staining and again after staining with SYBR Gold (Thermo) on an AlphaImager 3400.

Examples 5-7 below were primer extension experiments using the above procedure.

Example 5

Primer extension with compound 31 of the present disclosure.

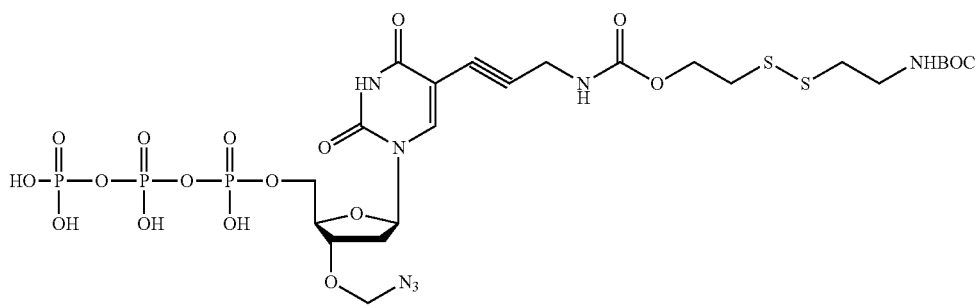

Compound 31

Figure 12:
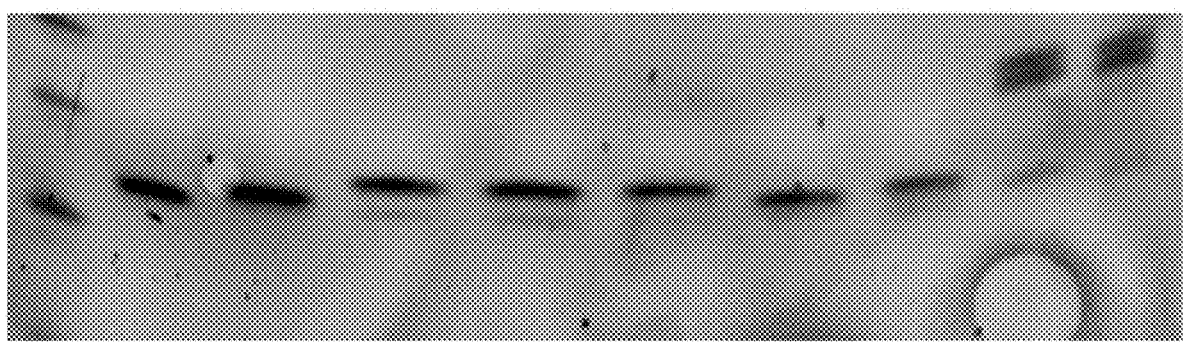
FIG. 12 Primer extension with compound 31 of the present disclosure into a growing DNA chain.

Primer extension was carried out using compound 31 of the present disclosure. The extension was catalyzed by an enhanced DNA polymerase ("EDP") and another DNA polymerase ("CENT1"). (See, FIG. 12). Compound 31 does not have a fluorophore. De-blocking was accomplished by incubation with TCEP.

Example 6

Primer extension with compound 33 of the present disclosure.

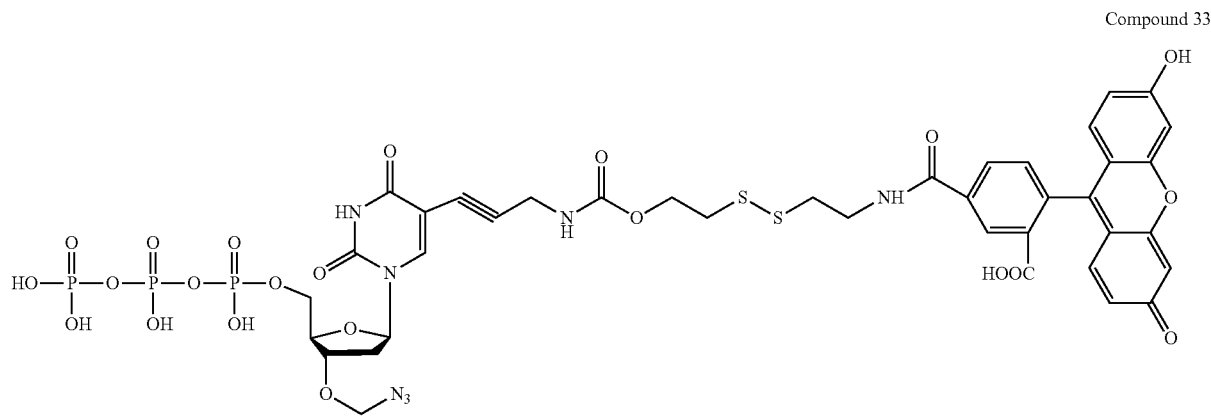

Compound 33

Figure 13:
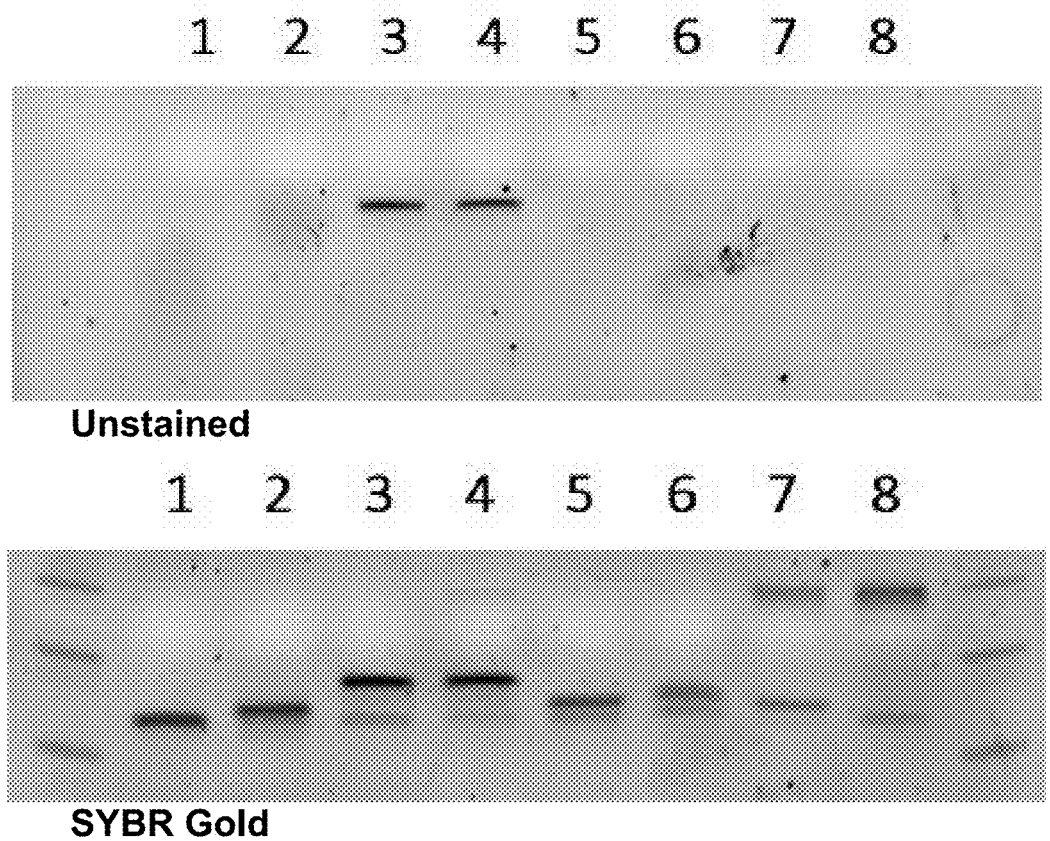
FIG. 13 Primer extension with compound 33 of the present disclosure into a growing DNA chain.

Primer extension was carried out using compound 33 of the present disclosure. The extension was catalyzed by a DNA polymerase ("CENT1"). (See, FIG. 13). Blocking of further extension after terminator incorporation is observed in a "runaway" reaction with Bst polymerase (See, lane 4). De-blocking was accomplished by incubation with TCEP with Bst polymerase and all four unmodified dNTPs. (See, lane 7).

Example 7

Primer extension with compound 34 of the present disclosure.

Figure 14:
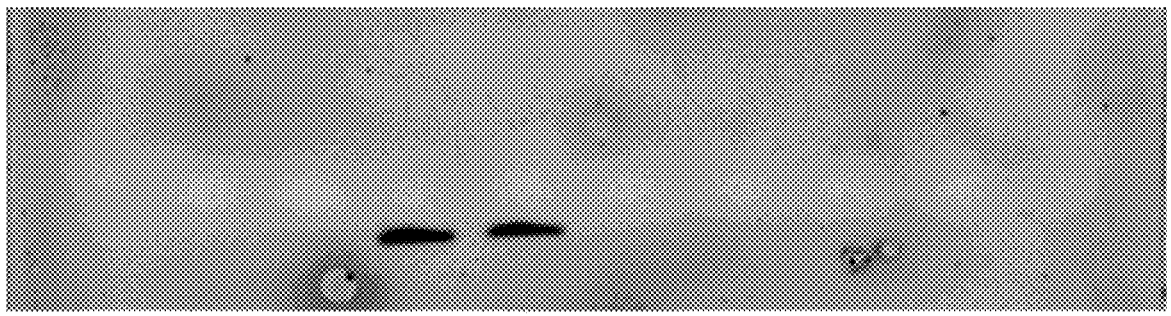
FIG. 14 Primer extension with compound 34 of the present disclosure into a growing DNA chain.
Figure 14:
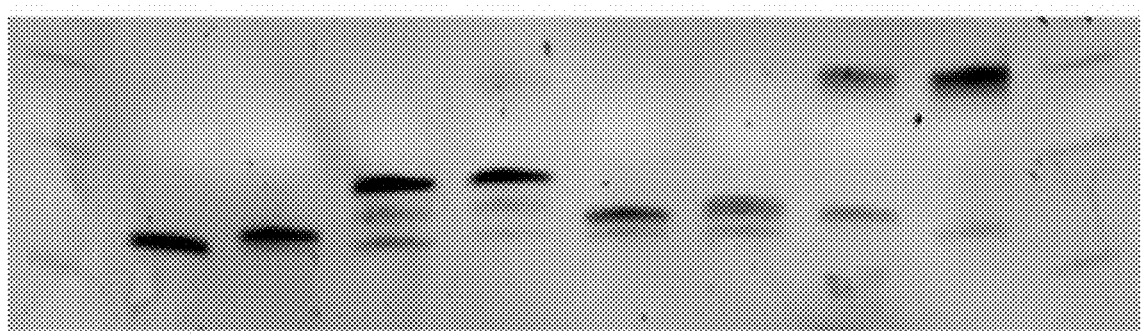

Primer extension was carried out using compound 34 of the present disclosure. The extension was catalyzed by an enhanced DNA polymerase ("CENT 1"). (See, FIG. 14). Blocking of further extension after terminator incorporation is observed in a "runaway" reaction with Bst polymerase (See, lane 4). De-blocking was accomplished by incubation with TCEP with Bst polymerase and all four unmodified dNTPs. (See, lane 7).

As shown in Examples 5-7 above, the reversible terminator of the present disclosure can be incorporated in primer extension reactions catalyzed by a DNA polymerase CENT1. For example, in 1 minute at 45° C. using 2 μM of the reversible terminator of the present disclosure and DNA polymerase CENT1, the reversible terminator of the present disclosure can be incorporated at the 3' terminus of the growing primer at about 100%. Further, Examples 5-7 showed that the incorporated reversible terminator can stop the polynucleotide extension (before the TCEP treatment); and after the TCEP treatment, which removed the azidomethyl capping group on the 3'-OH of the reversible terminator, the polynucleotide extension resumed.

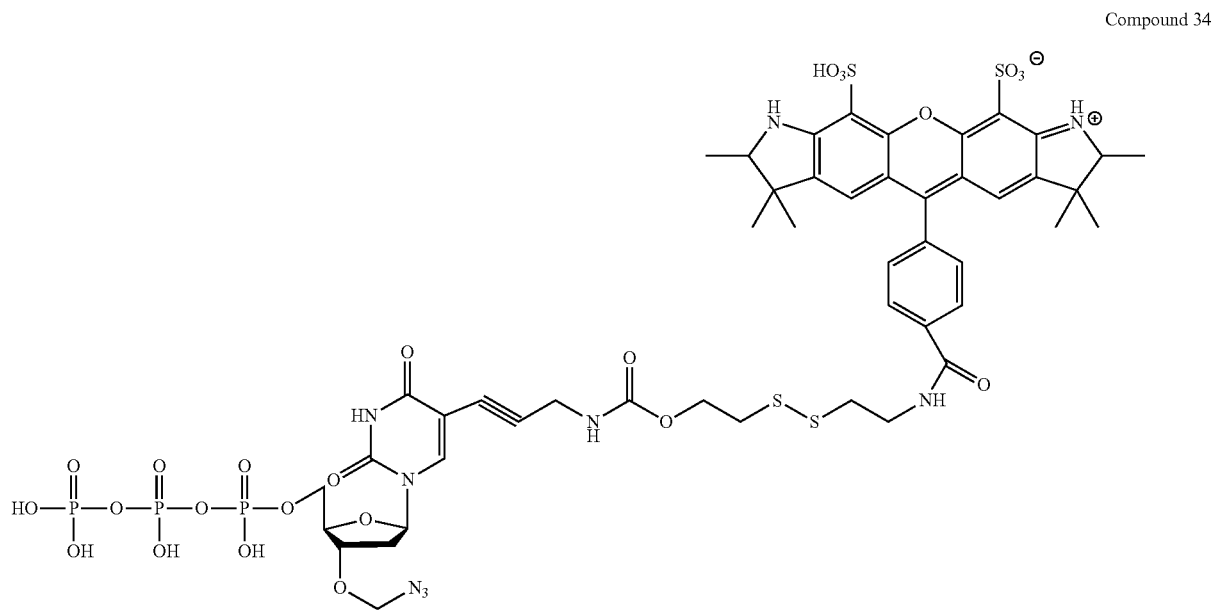

Compound 34

What is claimed is:

1. A nucleoside 5'-triphosphate analog according to formula (I):

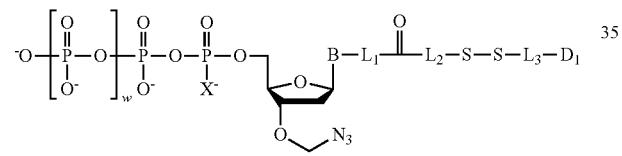

or a salt or protonated form thereof, wherein:

X is O, S, or $BH_3$;

w is 1, 2, 3, 4, or 5;

base B is selected from the group consisting of

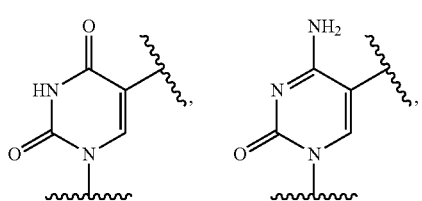

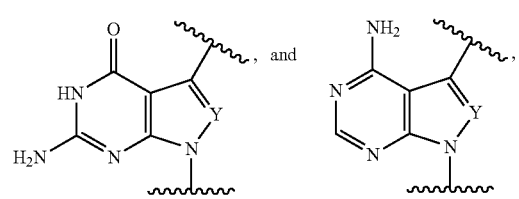

and Y is CH or N;

$L_1$ is a first linker group and $L_1$ is

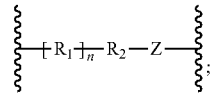

n is 0 or 1;

$R_1$ is

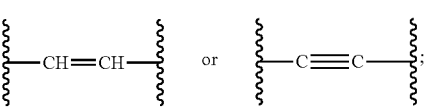

$R_2$ is

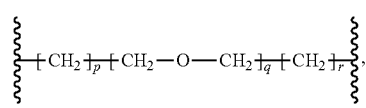

wherein p is 0-3, q is 0-12, r is 1-3; and

Z is O or NH;

$L_2$ is a second linker group and $L_2$ is

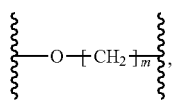

and m is 2 or 3;

$L_3$ is a third linker group and $L_3$ is

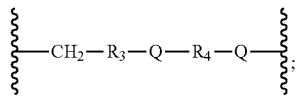

$Q_1$ and $Q_2$ are independently selected from the group consisting of none,

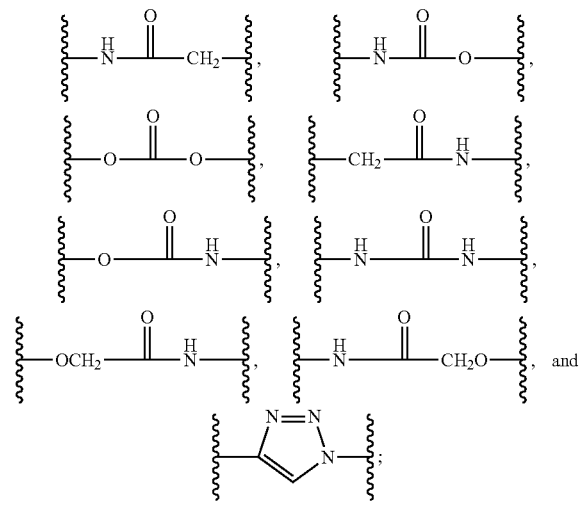

and
$R_3$ and $R_4$ are independently

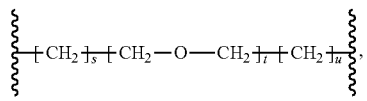

wherein s is 0-3, t is 0-12, and u is 1-3; and
$D_1$ is a label, wherein the label is a fluorophore and wherein the label is different for each different base B in a composition.

2. The nucleoside 5'-triphosphate analog of claim 1, wherein:
w is 1;
X is O;
$L_1$ is

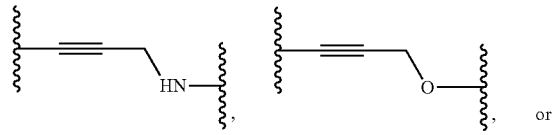

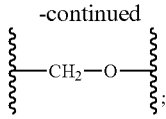

$L_2$ is

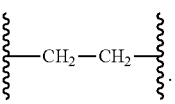

3. The nucleoside 5'-triphosphate analog of claim 1, wherein $D_1$ is a fluorophore.

4. A method of sequencing a polynucleotide, comprising: performing a polymerization reaction in a reaction system comprising a target polynucleotide to be sequenced, one or more polynucleotide primers which hybridize with the target polynucleotide to be sequenced, a catalytic amount of a polymerase enzyme and one, two, three, or four nucleoside 5'-triphosphate analogs of claim 1, wherein each of the one, two, three, of four nucleoside 5'-triphosphate analogs has a different Base selected from the group consisting of

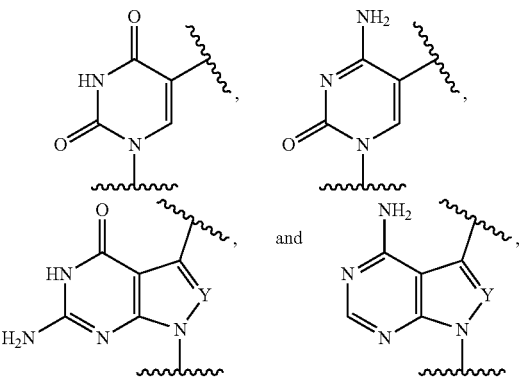

and Y is CH or N, thereby generating one or more sequencing products complementary to the target polynucleotide.

5. The method of claim 4, wherein the one, two, three, or four nucleoside 5'-triphosphate analogs of claim 1 at a concentration of no more than 100 μM.

6. The method of claim 4, wherein the one, two, three, or four nucleoside 5'-triphosphate analogs of claim 1 at a concentration of no more than 50 μM.

7. The method of claim 4, wherein the one, two, three, or four nucleoside 5'-triphosphate analogs of claim 1 at a concentration of no more than 10 μM.

8. The method of claim 4, further comprising: treating the one or more sequencing products with trialkylphosphine.

9. The method of claim 8, wherein the trialkylphosphine is tris(2-carboxyethyl)phosphine.

* * * * *

SEQUENCE LISTING

<160> NUMBER OF SEQ ID NOS: 2

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctgaacggt agcatcttga cgagatcgga agagcgtcgt gtagggaaag agtgtttcag    60

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
actctttccc tacacgacgc tcttccgatc tcg                                 33